United States Patent [19]

Martz

[11] Patent Number: 5,593,395
[45] Date of Patent: *Jan. 14, 1997

[54] VAPOR PERMEABLE DRESSING

[76] Inventor: Joel D. Martz, 5 Sealy Dr., Lawrence, N.Y. 11559

[ * ] Notice: The term of this patent shall not extend beyond the expiration date of Pat. No. 4,846,164.

[21] Appl. No.: 300,807

[22] Filed: Sep. 6, 1994

Related U.S. Application Data

[63] Continuation-in-part of Ser. No. 777,679, Oct. 15, 1991, abandoned, which is a continuation-in-part of Ser. No. 504,111, Apr. 3, 1990, Pat. No. 5,061,258, which is a continuation-in-part of Ser. No. 377,269, Jul. 10, 1989, abandoned, which is a continuation-in-part of Ser. No. 83,690, Aug. 7, 1987, Pat. No. 4,846,164.

[51] Int. Cl.[6] .................................................. A61F 13/00
[52] U.S. Cl. ............................ 604/304; 604/307; 602/58
[58] Field of Search ................................. 602/42, 43, 44, 602/45, 46, 54, 56, 58; 604/378, 289, 304, 307; 128/888

[56] References Cited

U.S. PATENT DOCUMENTS

| | | |
|---|---|---|
| Re. 31,886 | 5/1985 | Hodgson . |
| Re. 31,887 | 5/1985 | Hodgson . |
| 2,703,083 | 3/1955 | Gross . |
| 2,949,443 | 8/1960 | Merriam et al. . |
| 3,018,881 | 1/1962 | Wall . |
| 3,387,077 | 6/1986 | Sammons et al. . |
| 3,425,412 | 2/1969 | Pope . |
| 3,459,579 | 8/1969 | Newman . |
| 3,616,156 | 10/1971 | Scholl . |
| 3,645,833 | 2/1972 | Figge . |
| 3,774,592 | 11/1973 | Lahr . |
| 3,800,792 | 4/1974 | McKnight et al. . |
| 3,827,625 | 8/1974 | Miller .......................................... 229/62 |
| 3,842,832 | 10/1974 | Wideman et al. . |
| 3,939,237 | 2/1976 | Naito et al. . |
| 3,972,328 | 8/1976 | Chen . |
| 4,043,331 | 8/1977 | Martin et al. ............................... 602/42 |
| 4,077,410 | 3/1978 | Butterworth et al. ....................... 602/45 |
| 4,105,737 | 8/1978 | Suzuki . |
| 4,285,338 | 8/1981 | Lemelson . |
| 4,381,326 | 4/1983 | Kelly . |
| 4,390,387 | 6/1983 | Mahn . |
| 4,413,621 | 11/1983 | McCracken et al. . |
| 4,414,970 | 11/1983 | Berry ......................................... 602/75 |
| 4,452,845 | 6/1984 | Lloyd et al. . |
| 4,483,965 | 11/1984 | Ohba et al. . |
| 4,484,574 | 11/1984 | Derusha . |
| 4,485,809 | 12/1984 | Dellas . |
| 4,556,066 | 12/1985 | Semrow . |

(List continued on next page.)

FOREIGN PATENT DOCUMENTS

| | | | |
|---|---|---|---|
| 0353972 | 2/1990 | European Pat. Off. ............... 602/55 |
| 2425240 | 12/1979 | France . | |
| 2197590 | 5/1988 | United Kingdom . | |

Primary Examiner—Randall L. Green
Assistant Examiner—Perry E. Van Over
Attorney, Agent, or Firm—David M. Warren

[57] ABSTRACT

A water vapor permeable dressing, such as a surgical dressing, is constructed of a thin elastomeric transparent film which is protected by a layer of non-woven fabric, such as a material of elastomeric filaments. The fabric is sufficiently thin, elastic and fluffy to absorb stress of abrasive objects so as to protect the underlying film. Both the film and the protective fabric are sufficiently thin and compliant to allow the dressing to conform to the contours of the human body. Adhesive used in the dressing, for securing the film to a person's skin, as well as for securing the fabric to the film, are permeable to water vapor. The film and the adhesives are impermeable to liquid water, thereby to provide an effective shield for a wound against infection by outside bacteria. A release sheet is employed for protecting a layer of adhesive on the film. The release sheet has a topical reagent, such as a drug or medicine, imprinted thereon with a relatively loose bonding force such that, upon separation of the release sheet from the adhesive layer, the reagent is retained on the adhesive layer for subsequent contact with the skin of a patient to allow for topical application of the reagent to the patient via the skin. The release force may be varied by a coating pattern.

58 Claims, 8 Drawing Sheets

U.S. PATENT DOCUMENTS

| | | |
|---|---|---|
| 4,596,738 | 6/1986 | Metcalfe et al. . |
| 4,598,004 | 7/1986 | Heinecke . |
| 4,614,183 | 9/1986 | McCracken et al. . |
| 4,614,644 | 10/1986 | Saferstein et al. . |
| 4,619,253 | 10/1986 | Anhauser et al. . |
| 4,641,643 | 2/1987 | Greer . |
| 4,643,180 | 2/1987 | Feld et al. . |
| 4,649,909 | 3/1987 | Thompson . |
| 4,699,792 | 10/1987 | Nick et al. . |
| 4,706,662 | 10/1987 | Thompson . |
| 4,781,293 | 11/1988 | Johns . |
| 4,815,457 | 3/1989 | Mazars et al. . |
| 4,846,164 | 7/1989 | Martz . |
| 4,850,990 | 7/1989 | Huntoon et al. . |
| 4,867,150 | 9/1989 | Gilbert . |
| 4,884,563 | 12/1989 | Sessions . |
| 4,913,138 | 4/1990 | Yoshida et al. . |
| 4,926,850 | 5/1990 | Lott et al. . |
| 5,042,466 | 8/1991 | McKnight . |
| 5,061,258 | 10/1991 | Martz . |

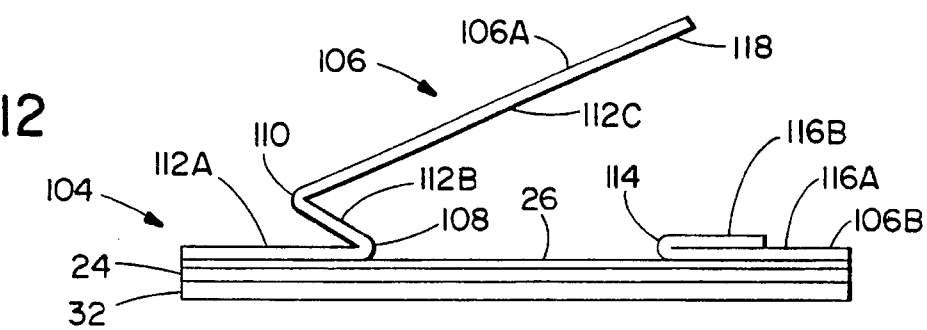
FIG. 12
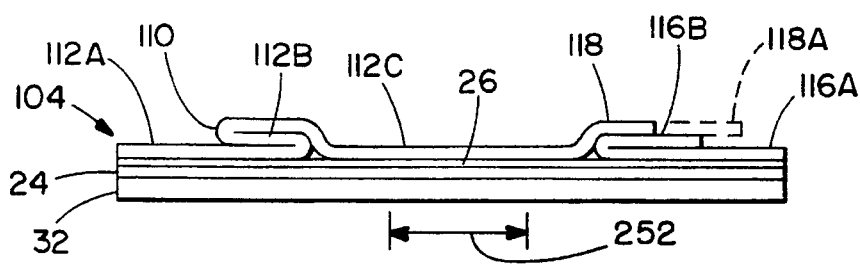
FIG. 13
FIG. 14
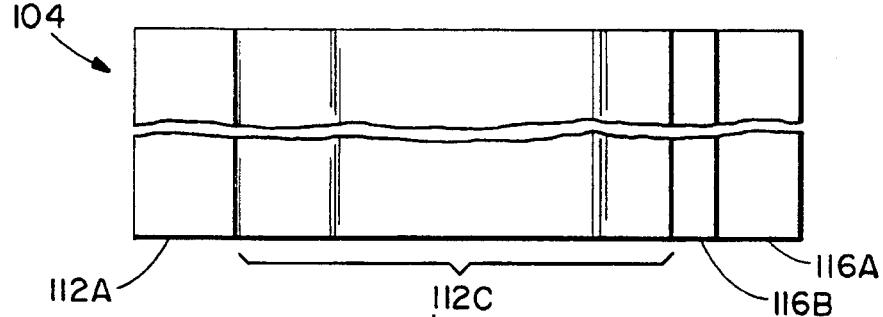
FIG. 15
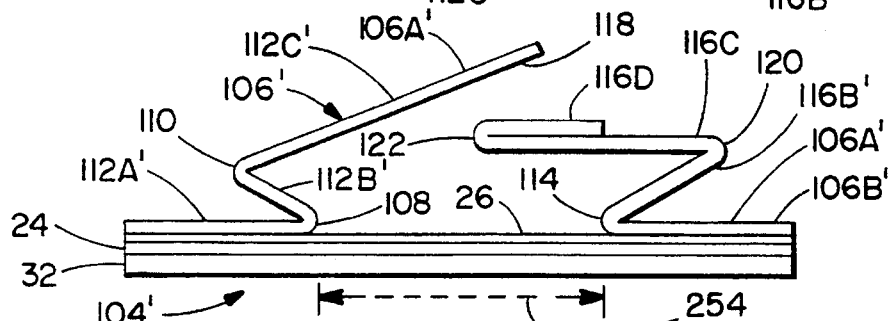
FIG. 16
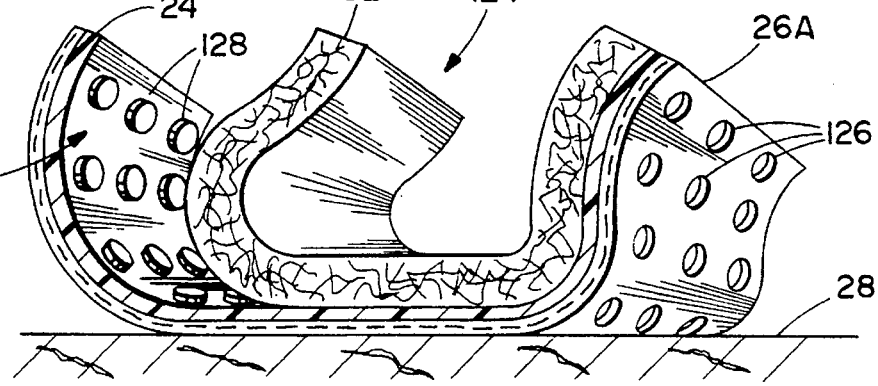

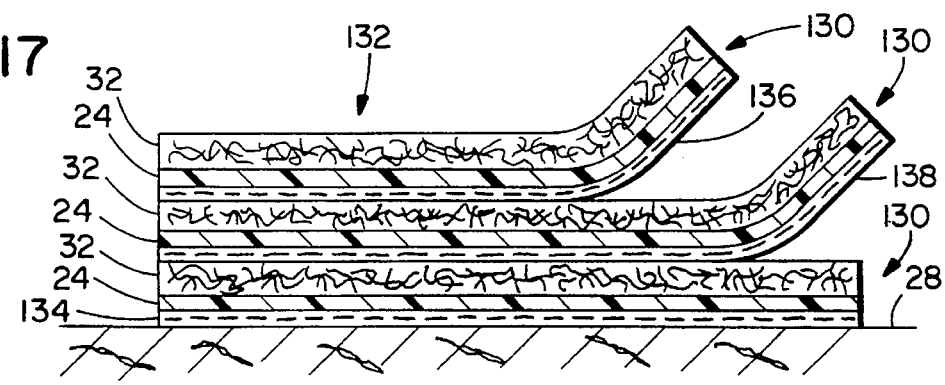
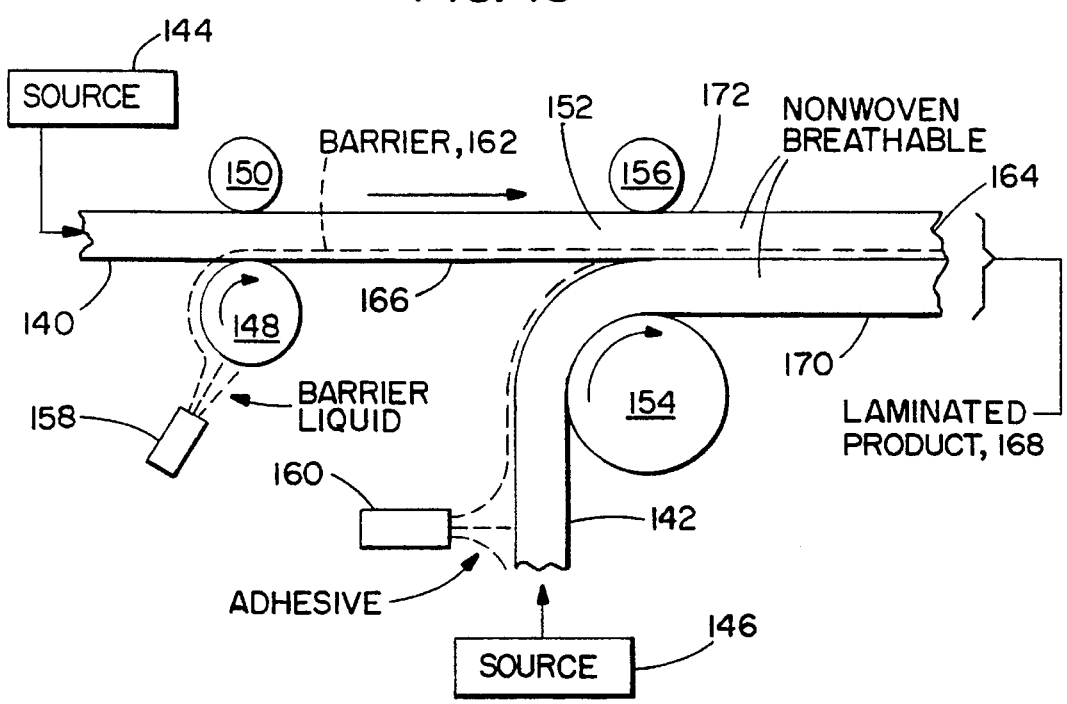
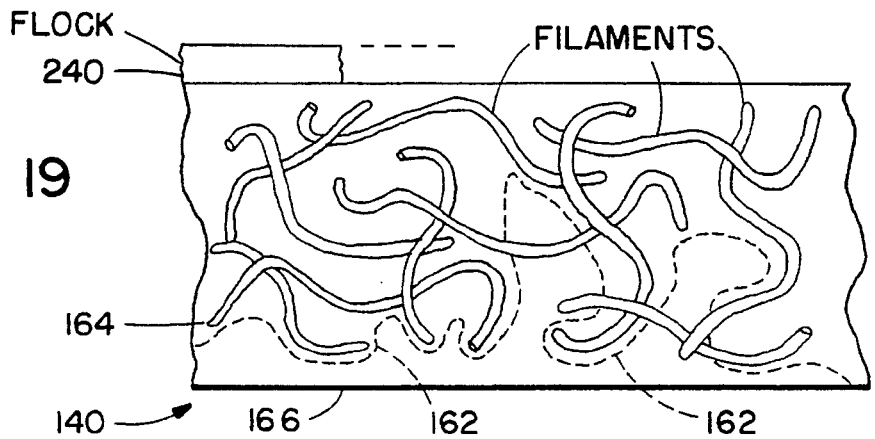

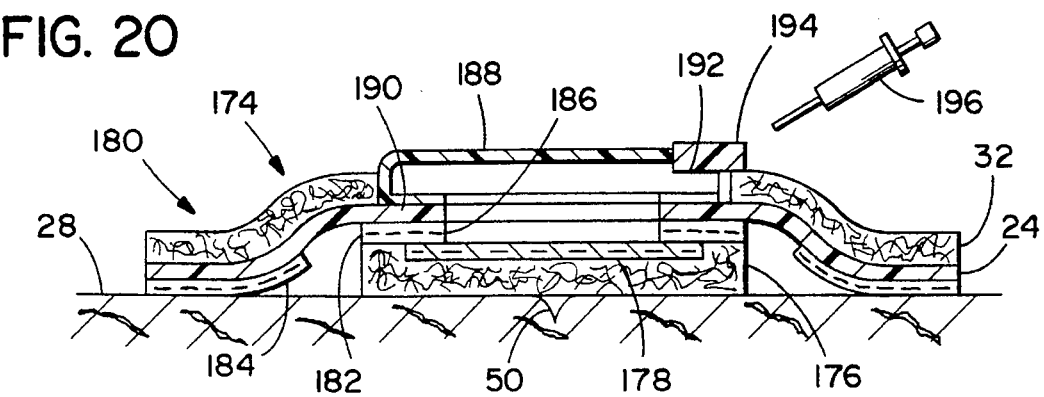
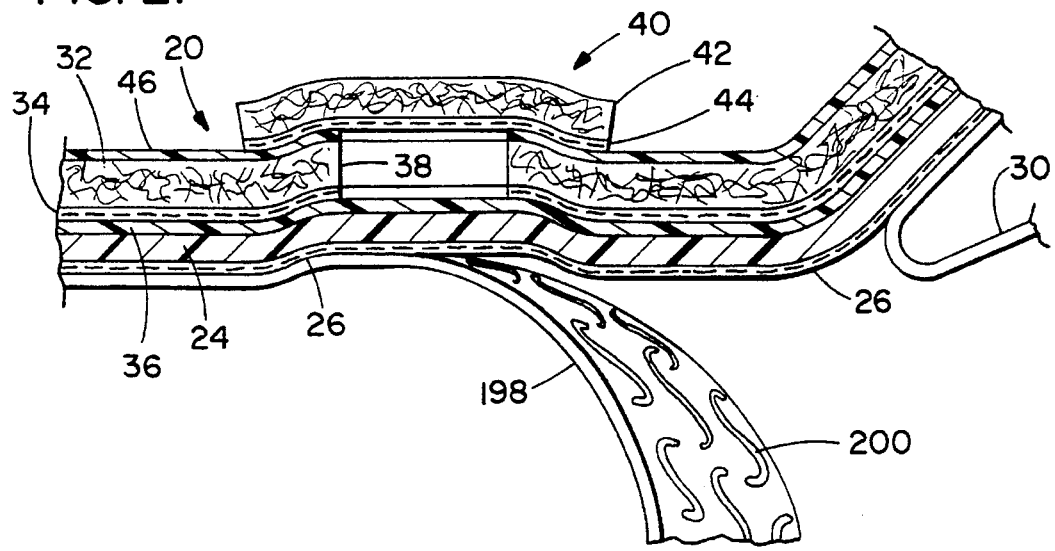
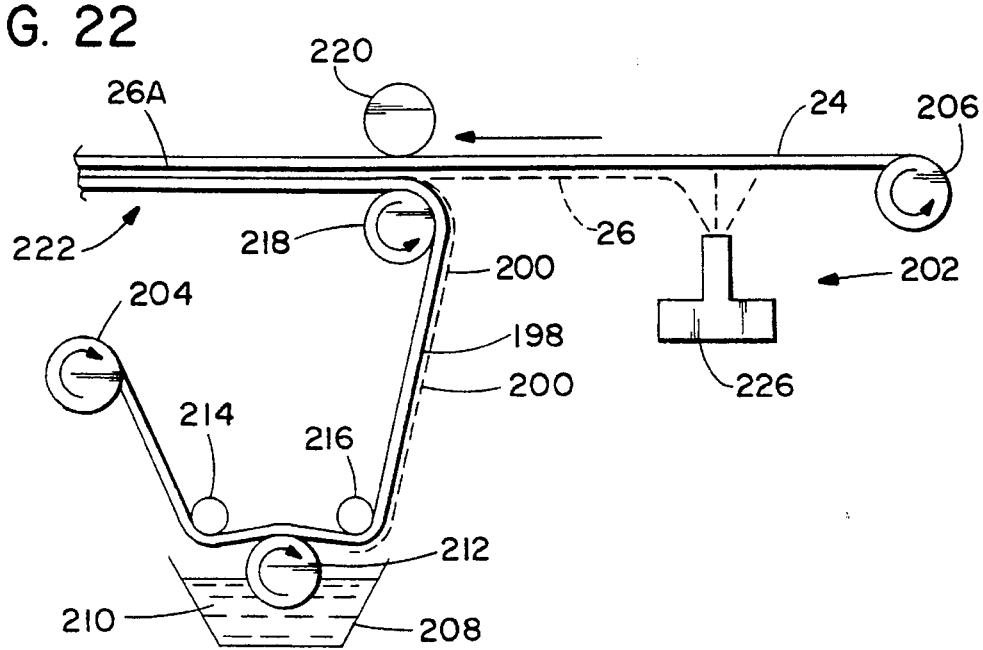

FIG. 23
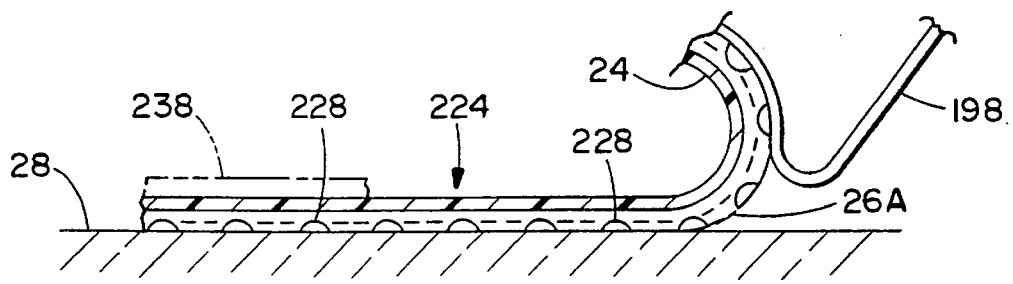
FIG. 24  FIG. 25  FIG. 26
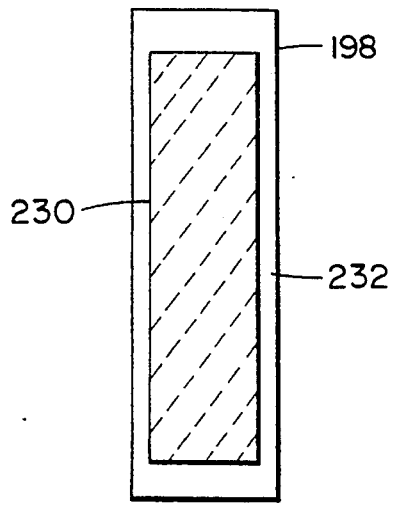 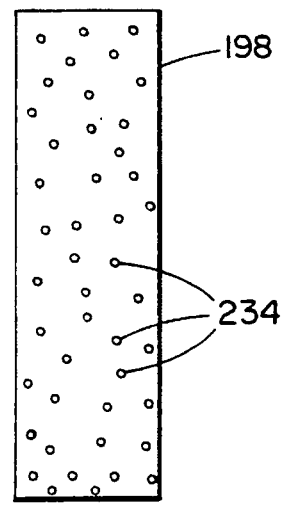 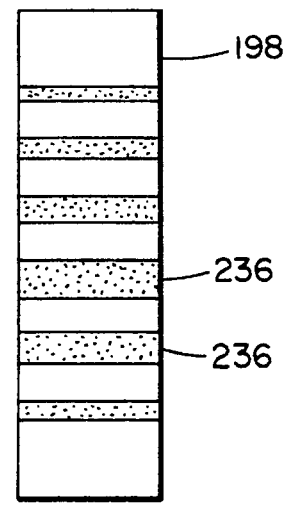

VAPOR PERMEABLE DRESSING

RELATED APPLICATIONS

This application is a continuation-in-part of application Ser. No. 07/777,679 filed Oct. 15, 1991, now abandoned, which is a continuation-in-part of application Ser. No. 07/504,111 filed Apr. 3, 1990, now U.S. Pat. No. 5,061,258 issued Oct. 29, 1991, which is a continuation-in-part of application Ser. No. 07/377,269 filed Jul. 10, 1989, abandoned, which is a continuation-in-part of original application having Ser. No. 07/083,690 filed Aug. 7, 1987, now U.S. Pat. No. 4,846,164 issued Jul. 11, 1989.

BACKGROUND OF THE INVENTION

This invention relates to moisture vapor permeable film dressings for covering wounds on human and animal skin, and, more particularly, to a structure of a thin transparent moisture vapor permeable film dressing with a moisture vapor permeable adhesive, there being a vapor permeable protective fabric which may be secured to the film on a side opposite the adhesive to facilitate manipulation of the dressing, and to provide the thin film with protection from abrasion. A drug or medicine for topical application may be included within the adhesive. The dressing may include optionally a pad on the adhesive side of the film for absorption of body exudate. The composite structure of the film and the protective fabric, such as a nonwoven filamentary fabric, is sufficiently thin and elastic to readily conform to the shape of a body being draped by the dressing.

The use of thin films on the order of one mil thickness, which are impermeable to liquid water but permeable to water vapor is finding increased use in the construction of surgical dressings. Such dressings may include the film with or without a gauze pad or other absorptive plus some form of backing layer to facilitate emplacement of the dressing on the wound. Occasionally, the dressing is completed by use of gauze or other fabric which covers the film so as to protect the fragile film from abrasion and/or puncture by foreign objects which may contact the patient wearing the dressing.

The use of the thin film is advantageous for a number of reasons. The film is impermeable to liquid water and to bacteria so as to form a very effective shield which protects a patient from sources of infection external to the skin. The film retains body fluids within the body at the site of the wound. The vapor permeability of the film provides a sufficient rate of water vapor transport through the film to allow the skin to breathe normally. The film has sufficient elasticity to conform to the shape of various parts of the body, even a flexible body part such as a knee or elbow. Both the film and the adhesive layer may be constructed to be transparent, such transparency permitting the physician to observe the wound area without removal of the dressing. The material of the dressing is non-allergenic. The foregoing characteristics of the dressing permit the dressing to be kept in place for significantly longer periods of time than with other non-film types of dressings, this resulting in a great convenience to both the patient and attending medical staff, and also providing for better healing in some types of breaks in the integument, incisions, or wounds and providing better cost effectiveness in medical practice due to decreased need for dressing changes.

Such moisture vapor permeable films may be made from synthetic polymers and formed by casting, extrusion or other known film-making processes. Film thickness is in a range of typically 0.5–10 mils and preferably in a range from 0.6–3 mils. The film is continuous in that it has no perforations or pores which extend through the depth of the film. Films of this type are known and generally are hydrophilic polymeric materials through which water vapor is capable of diffusing. The films are formed of plastic material such as polyurethane or arylate copolymers, see McCracken et al, U.S. Pat. No. 4,413,621. A suitable adhesive for securing the thin film to human skin is disclosed in Hodgson, U.S. Pat. No. 3,645,835 (now U.S. Pat. No. Re. 31,886 and 31,887). Generally, these films have moisture vapor transport rates between 15 and 80 grams per 100 square inches per 24 hour interval at 100° Fahrenheit and 90% Relative Humidity.

In spite of the many advantages of the thin film, there are problems associated with its use. The film is too thin to be handled without some form of backing sheet or release sheet because the extreme flexibility and limpness allow the film to curl over upon itself. Furthermore, in the presence of an adhesive layer on one surface of the film, the film may stick to itself, this presenting great difficulty in applying the film to a patient. While the feature of transparency is most beneficial in allowing a physician to observe the wound, this feature is distressing to a patient who would prefer not to look at an ugly wound. The film, because of its extreme thinness, is fragile, and can readily catch on a sharp or rough object resulting in a tearing of a dressing constructed of the film.

If an attempt be made to overcome the foregoing difficulties by use of a permanent backing layer of greater stiffness and resistance to abrasion, then a further problem is introduced, namely, such backing layer would materially alter the vapor transport rate of the dressing and might not allow any vapor transport. If an opaque covering, such as a cloth bandage, be placed over the film to occlude the distressing view of the wound from the patient, then the disadvantage is introduced in that an attending physician must remove the cloth covering in order to view the wound. Also, such dressings have not taken advantage of an opportunity for topical administration of medicine to a patient.

SUMMARY OF THE INVENTION

The aforementioned problems are overcome and other advantages are provided by a thin dressing which, in accordance with the invention, is fabricated of a thin film of polyurethane or other similar elastomeric polymer or copolymer having an adhesive layer on one surface and a nonwoven fabric secured to the opposite surface. The composite structure of adhesive layer, film and nonwoven fabric is permeable to water vapor and has a sufficiently high transport rate of the vapor to permit the skin of a patient receiving the dressing to aspirate water vapor normally through the dressing. The film and the adhesive layer are transparent. The nonwoven fabric is opaque, and is constructed as a spun-bonded elastic material. Alternatively, the nonwoven fabric may also be constructed as a highly perforated elastic film of material similar to the foregoing thin film, the large amount of perforation permitting the transport of water vapor without adding any significant resistance to the vapor flow. The nonwoven elastic fabric has an extensive amount of voids passing completely through the fabric which allows passage of both liquid water and water vapor. However, the thin film is impervious to the liquid water so that the presence of spun-bonded material in no way reduces the protective barrier of the thin film to infection. The nonwoven fabric has recoverable elastic strain at least double the unstrained length, the elasticity and recoverability being multidimensional so as to be conformable to body contours and provides unhindered full range of motion on joints of a patient wearing the dressing.

It is an object of the invention to facilitate use of the dressing by an attending physician. It is a further object of the invention to reduce distress and introduce a measure of comfort to a patient wearing the dressing.

Use by an attending physician is facilitated by virtue of an inherent stiffness to the nonwoven fabric, which stiffness overcomes the tendency of the thin film to curl upon itself, the nonwoven fabric enabling the physician to readily manipulate the dressing for emplacement upon a wound. An elastic nonwoven fabric stretches along with the elastic film during positioning on the patient. A release sheet covers the adhesive layer until emplacement of the dressing upon the wound, at which time the release sheet is removed to expose the adhesive layer to the patient's skin. If desired, a gauze pad, foam or other absorptive device may be included within the dressing, the absorptive pad being positioned on the adhesive side of the film. The foregoing multiple laminate structure of the dressing is readily packaged, dispensed, and manipulated in a hospital situation.

The nonwoven fabric is bonded to the film by a fusing or by use of an adhesive. Such bonding retains the vapor transport characteristic of the dressing. The dressing may be constructed in a manner which allows the physician to view the wound without removal of the dressing. This is accomplished in one embodiment of the invention by the construction of a window in the fabric, and by adhesively securing a further layer of fabric over the window to act as a shade for opening and closing the window, thereby to show or hide the wound. Alternatively, the surface of the film facing the fabric may be provided with a release coat permitting an adhesively secured fabric to be retracted away from the film for viewing the wound, after which the fabric is restored to its original position upon the film. In the window-shade construction, a release coat may be placed on the outer surface of the fabric to facilitate lifting and replacement of the window shade.

In the use of the dressing on young children, children can be comforted in the distressing situation of a bodily wound by imprinting a colored likeness of a cartoon, animal, or other character upon the fabric. The shape of the final dressing may follow the contour of the imprint.

It is also noted that the nonwoven elastic fabric itself, due to its elasticity, its elastic recoverability, and its capacity for allowing skin to breathe, can be used as an elastic bandage, as for binding a sprained joint. The fabric can be much thinner than currently employed woven or knitted fabrics for this purpose and still retain adequate strength for use in binding sprained joints. This is particularly advantageous in the case of a binding of a sprained ankle because the fabric is thin enough to be worn within a shoe.

The elastic properties of the nonwoven material can also be employed for fabricating an elastic bandage. Since the nonwoven material is in the nature of a plastic such as polyurethane which, while being transmissive to sweat does not absorb sweat, increased comfort to a wearer of the bandage is attained by flocking the nonwoven material with particles of a material such as cotton or rayon which absorbs sweat. The permeability of the nonwoven material to moisture absorbed by the cotton or rayon prevents excessive buildup of moisture in the flocking so as to maintain the comfortably dry feeling to the wearer.

Additional advantageous features of the invention are attained by the use of a release sheet formed in two sections which cover an adhesive side of a dressing, at least one of the sections of release sheet having a reverse fold to allow a nurse or other person employing the dressing to apply the dressing more readily to a patient's skin. The reverse fold is operative to signal the nurse, by cessation of force between sheet and adhesive, that the section of sheet has cleared the adhesive in the central portion of the dressing. In this way, the sheet serves to stiffen the dressing prior to application of the dressing, thereby to facilitate manipulation of the dressing. As the dressing is held in both hands of the nurse, one hand holding the folded section of fabric and the other hand holding the partially unfolded section of fabric, the film of the dressing can be applied directly to the patient's skin without buckling or twisting the film. This arrangement of the release sheet can be employed both with a simple film dressing as well as with a laminated dressing of film and nonwoven material.

A further feature of the invention is the use of two adhesive layers employing a pattern or perforations or windows and a pattern of islands of adhesive. The layer of adhesive employed in securing film to the patient's skin is provided with perforations or windows in the adhesive for increased capacity to breath The adhesive layer employed between the film and the nonwoven material is formed of spaced-apart islands of adhesive which serve the dual functions of improved breathing capacity and reduction of adhesive strength in those situations where it is desirable to temporarily separate the nonwoven material from the film, as for viewing a wound. This technique of spaced-apart islands of adhesive can also be employed in a dressing having multiple layers of film and nonwoven material to enable selective reduction or enlargement in the number of layers of material so as to select a desired capacity to breathe.

In yet a further aspect of the invention, the film can be dispensed with, and replaced with a barrier to liquid water formed directly upon and within interstices of the woven material. The barrier is permeable to water vapor and is formed of the same material as is employed in the construction of the film. However, the barrier, which is formed by deposition of polymer material directly on the nonwoven material and is drawn into interstices by forces of rheology, can be substantially thinner than that which can be obtained in the use of a film, thereby to allow for a much greater capacity to breathe. If desired, a further layer of nonwoven material can be applied alongside a surface of the first-mentioned layer of nonwoven material, alongside the barrier, to locate the barrier centrally within a mass of nonwoven material which can act as an absorber of water, while the barrier acts to retain the water within the nonwoven material. A single layer of nonwoven material with the barrier therein is suitable for use as a dressing, and can also be employed in other situations requiring a covering, such as for the entrapment of liquid exudate. The breathability of the barrier allows the covering to be used for purposes other than a dressing, such as in industry for various industrial processes. Also, the covering can be employed in the nature of a garment, such as a diaper, for absorbing liquid and for storing the liquid.

A particularly useful aspect of the invention relates to the administering of a reagent such as a drug, medicine or other active ingredient to a patient via the skin of the patient, a reagent suitable for such form of administration being referred to as a topical reagent. This is accomplished by imprinting the topical reagent upon a release sheet, and then employing the release sheet to cover an adhesive layer upon the vapor-permeable film. The adhesive layer is made available for securing the film to the patient by removal of the release sheet. However, upon removal of the release sheet, the adhesive forces of the adhesive layer retain the reagent upon the adhesive layer by separating the reagent from the release sheet. Then, upon a securing of the film to the patient by the adhesive layer, the reagent is placed in contact with the patient's skin, and held upon the skin for a sufficient length of time to allow the reagent to be absorbed by the skin. The reagent can be imprinted as a continuous coating, or in patterns of various shapes including, a random distribution of dots, a repeating pattern of various contours, and a non-repeating pattern.

BRIEF DESCRIPTION OF THE DRAWING

The aforementioned aspects and other features of the invention are explained in the following description, taken in connection with the accompanying drawing wherein:

FIG. 12 shows a side view of a dressing formed of nonwoven material secured to a breathable film with an adhesive side of the film secured to two sections of flexible release sheet which are employed to cover the adhesive, one of the pieces of sheet having a reverse fold, the view showing a piece of release sheet partially lifted away from the film;

FIG. 13 shows the dressing of FIG. 12 with the release sheet fully secured to the adhesive side of the film;

FIG. 14 shows a plan view of the dressing of FIG. 13;

FIG. 15 shows an alternative embodiment of the dressing of FIG. 12 wherein both pieces of release sheet are provided with a reverse fold;

FIG. 16 shows a dressing formed of a layer of nonwoven material secured to a film, edges of the dressing being shown curled up and retracted from a patient's skin to show an adhesive layer with perforations therein, the nonwoven material and the film being shown separated at an opposite end of the dressing to disclose an adhesive layer formed of spaced-apart dots or islands of adhesive;

FIG. 17 shows a laminated dressing having plural layers of nonwoven material and plural layers of film wherein adhesives of differing strength are employed between various sections of the laminated dressing to allow removal of sections or addition of more sections to adjust a rate of vapor transport through the dressing;

FIG. 18 shows a manufacture of a covering, suitable for use as a medicinal or surgical dressing as well as for other purposes including manufacturing processes, the covering being formed of a layer of nonwoven material with a vapor-permeable barrier to liquid water being formed by deposition of a liquid polymer within the layer of nonwoven material, the figure showing also the adhesion of a second layer of nonwoven material to the first layer adjacent the barrier;

FIG. 19 is an enlarged, stylized, fragmentary view of a section of the nonwoven material incorporating the barrier of FIG. 18;

FIG. 20 is a stylized sectional view of a dressing adapted for aseptic topical delivery of medication;

FIG. 21 is a stylized view of a dressing, similar to that of FIG. 2, demonstrating the replacement of a plain release sheet with a second release sheet which has been imprinted with a topical reagent, a portion of the release sheet being twisted to show a periodic pattern of contours of the topical reagent;

FIG. 22 is a diagrammatic view of apparatus for imprinting a pattern of topical reagent on a release sheet, and combining the release sheet with a vapor permeable film by means of an adhesive layer disposed between the sheet and the film;

FIG. 23 shows a vapor permeable film secured by an adhesive layer to the skin of a patient, the adhesive layer including pockets of topical reagent along an interface of the adhesive layer with the skin;

FIG. 24 is a plan view of a release sheet with a central region covered continuously with topical reagent, indicated diagrammatically, the central region being surrounded by a margin void of the reagent;

FIG. 25 is a release sheet having topical reagent disposed along the entire sheet in a random pattern of small dots;

FIG. 26 is a plan view of a release sheet having topical reagent imprinted thereon, the topical reagent being indicated diagrammatically and being arranged in a non-repeating pattern of varying width;

DETAILED DESCRIPTION

Figure 1:
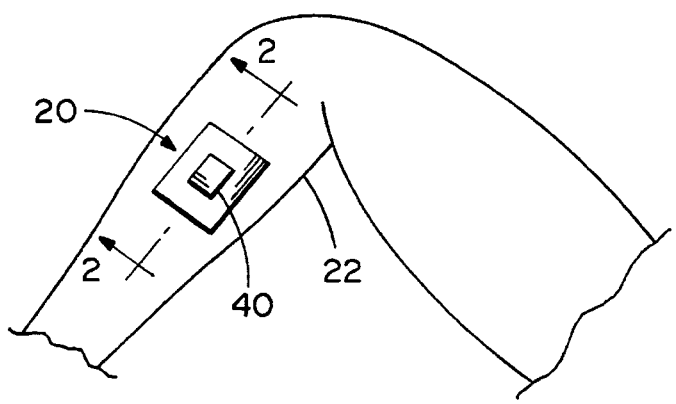
FIG. 1 shows a stylized view of a portion of a person's arm having a dressing thereon, the dressing being constructed in accordance with the invention.
Figure 2:
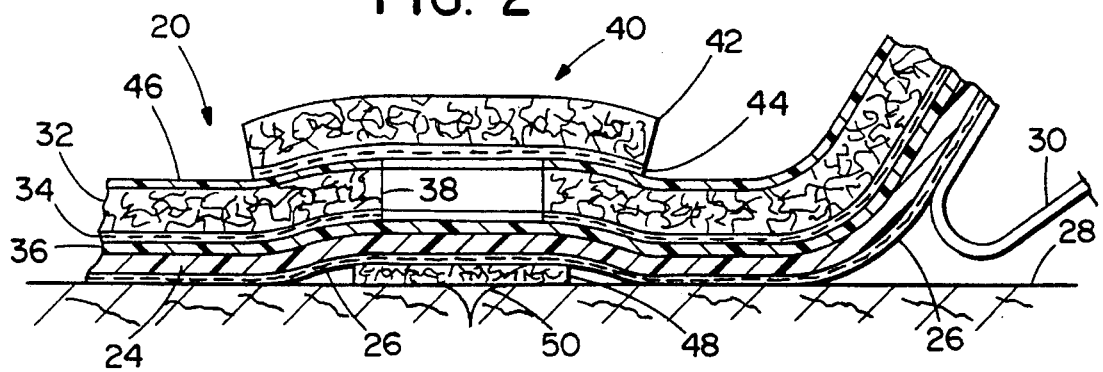
FIG. 2 shows a cross-sectional view of the dressing taken along the line 2—2 in FIG. 1.

With reference to FIGS. 1 and 2, a dressing 20 is applied to an arm 22 of a patient. The dressing 20 is constructed in accordance with the invention, and includes a film 24 having a first adhesive layer 26 for securing the dressing 20 to skin 28 of the patient. The dressing 20 is provided with a release sheet 30 such as siliconized paper which covers the adhesive layer 26 prior to use of the dressing 20. The release sheet 30 is shown partially removed in FIG. 2, such removal being accomplished to expose the adhesive layer 26 during emplacement of the dressing 20 upon the patient's arm 22.

The dressing 20 further comprises a layer 32 of fabric which, in a preferred embodiment of the invention, is formed of a sheet of nonwoven elastic material such as a spun-bonded material or a multiply perforated sheet of plastic. The fabric layer 32 is bonded to a second surface of the film 24 opposite the first adhesive layer 26 by fusing or, as shown in FIG. 2, by a second layer 34 of adhesive. The second surface of the film may be provided with a release coat 36 which cooperates with the second adhesive layer 34 to facilitate partial or complete removal of the fabric to enable a physician attending the patient to view the portion of the skin 28 covered by the dressing 20. After such viewing, the fabric is returned to its position on the film 24 and held in that position by the second adhesive layer 34.

The dressing 20, as described so far, constitutes a first embodiment of the invention which is capable of protecting an area of the skin from infection, and which permits a viewing of the region of the skin beneath the dressing 20 by releasably securing the fabric to the film 24 by an attending physician. The fabric layer 32 is opaque so as to hide the wound, skin and any discoloration or exudate which may be produced by the patient.

By way of further embodiment of the dressing 20, a window 38 can be formed within the fabric layer 32 by cutting away a portion of the fabric layer 32 having the desired shape, typically round or square, of the window 38. The window 38 permits a viewing of the skin without removal of the layer of fabric layer 32. In order to protect the portion of the film 24 bounded by the window 38, and to close off the window 38 from a viewing by the patient, a window shade 40 is removably secured about the window 38. The shade 40 comprises a flap 42 of the fabric and a third adhesive layer 44 which secures the shade 40 to the top surface of the fabric layer 32. The top surface of the fabric layer 32 may be provided with a release coat 46 to facilitate removal of the shade 40, and to permit the shade 40 to be replaced and secured by the adhesive layer 44 to the fabric layer By way of further embodiment, a gauze pad 48 of cotton or other absorbent material may be secured to the first side of the film 24 for absorbing exudate from a wound 50 in the skin 28. The window 38 permits a viewing of the pad 46 so as to determine how much oozing of body fluids may have occurred at the site of the wound 50.

Figure 3:
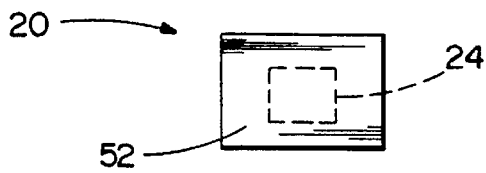
FIG. 3 shows a plan view of an embodiment of the dressing wherein nonwoven fabric extends beyond the perimeter of the film.
Figure 4:
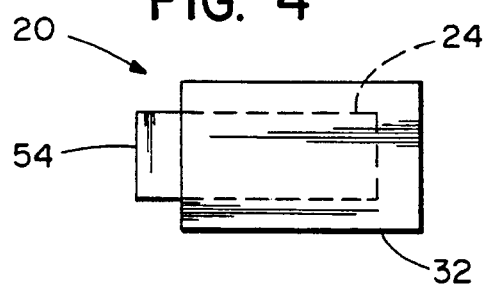
FIG. 4 shows an embodiment of the invention wherein a part of the film protrudes as a tab from underneath the nonwoven fabric.

FIGS. 3 and 4 show further configurations of the dressing 20. In FIG. 3, the fabric 32 extends beyond the periphery of the film 24 to provide a border 52 which completely surrounds the film 24. This configuration is useful as a bandage which can be applied by a child to cover a wound. In the dressing 20 of FIG. 4, the film 24 is provided with a tab 54 which extends beyond an edge of the fabric 32. This facilitates a separation of the fabric 32 from the film 24 when it is desired to lift a portion of the fabric 32 for viewing the wound 50 or gauze pad 48.

Figure 5:
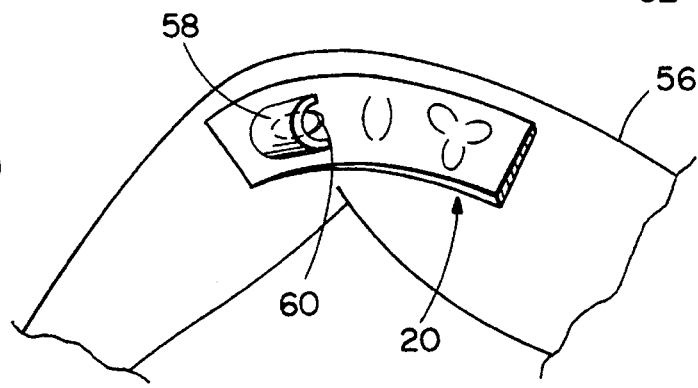
FIG. 5 shows a dressing in the form of a bandage with a cartoon sketched thereon, the cartoon showing a face wherein a mouth is placed at a point of flexure on a knee of a patient's leg to show an opening of the mouth when the leg is flexed; and wherein nonwoven fabric extends beyond the perimeter of the film.

With reference to FIG. 5, a feature of the invention is demonstrated by placing the dressing on a knee 56 of the patient. Therein, the dressing 20 is provided with a cartoon character printed directly on the surface of the fabric layer 32. Such a character is an aid to cheering children who may have undergone a surgical procedure and, by reducing mental stress associated with the recovery process, aids a return to good health. A particular feature of the cartoon embodiment of the dressing 20 is the emplacement of a mouth of the cartoon face at a point of flexure of the knee 56 so that, upon a bending of the knee 56, the mouth is stretched so as to appear to open. When the knee is brought to a straight position, the mouth appears to close. This is a useful feature, particularly in the case of young children, for enabling some measure of happiness to be introduced into their lives.

If desired, a pocket 58 can be created on the front surface of the fabric 32 by use of an additional layer of the fabric which is adhesively secured at edges thereof to the layer of fabric 32. A miniaturized music or sound-producing device 60 in the form of a button is placed within the pocket 58. Alternatively, in lieu of the music device 60, a sponge (not shown) of similar button shape may be placed within the pocket 58, the sponge, or other pad of liquid absorbent material, being saturated with a gel of a medicine which can be administered by contact with the skin of a patient. Liquid containing the medicine slowly passes from the sponge via the moisture permeable dressing 20 to the skin of the patient. If desired, the rate of passage of the medicine can be increased by cutting away a portion of the dressing 20 within the pocket 58. The dressing with the sponge-like material in the pocket 58 may be regarded as a trans-dermal medication patch useful for the slow administration of a drug such as nitroglycerin.

Figure 6:
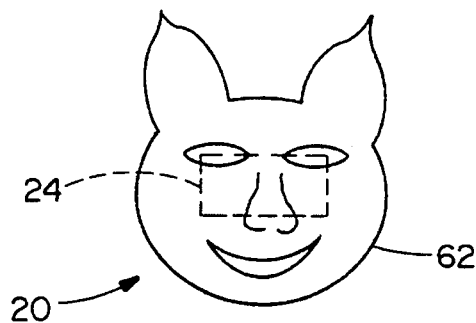
FIG. 6 shows a dressing formed as bandage which can be dispensed by a child, a periphery of the nonwoven fabric extending beyond the periphery of the film and being shaped in the form of a cartoon wherein nonwoven fabric extends beyond the perimeter of the film.

In FIG. 6, the cartoon aspect of the dressing 20 is embellished still further by extending the fabric of the layer 32 well beyond the perimeter of the film 24, and by cutting the outer edge of the fabric to have the physical shape of a cartoon character. As used herein and in the claims, the term "cartoon" is not limited to only the facial configuration, but is intended to include shapes of other objects frequently found in children's literature, such as, rainbows, bells, and stars. Such a form 62 having an animal face and long ears is shown in FIG. 6. In addition, an outline of facial features is imprinted on the surface of the fabric to add further realism to the cartoon form 62.

Figure 7:
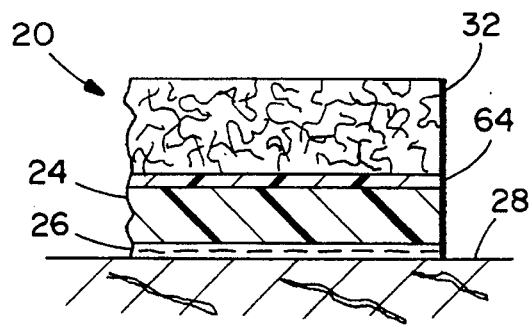
FIG. 7 is an enlarged fragmentary sectional view showing an edge of the dressing in an embodiment wherein the nonwoven fabric is fused to the film.
Figure 8:
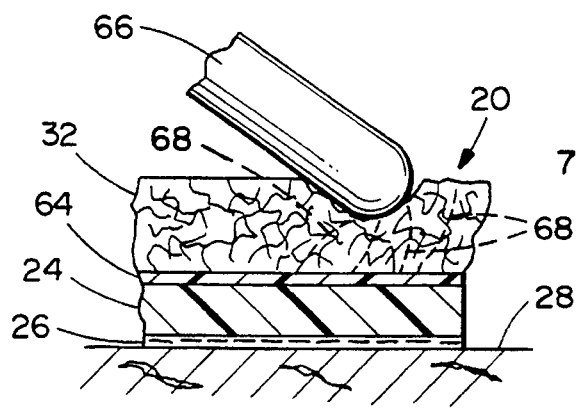
FIG. 8 shows the view of FIG. 7 under conditions wherein the nonwoven fabric is being abraded by a pointed object such as a hairpin, FIG. 8 including a diagrammatic representation of lines of stress to demonstrate the distribution of stress about a large surface region of the film.

FIGS. 7 and 8 show an enlarged fragmentary view of an edge of a dressing 20 in accordance with the first embodiment of the invention comprising only the film 24 and the fabric 32 which serves as a protective layer for the film 24. In the structure disclosed in FIGS. 7 and 8, the fabric layer 32 is bonded to the film 24 by fusing, a region 64 of the fusing being indicated in FIG. 7.

Figure 9:
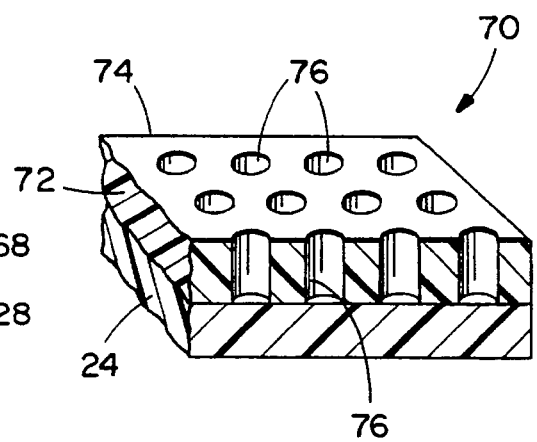
FIG. 9 is an enlarged fragmentary view of a dressing employing a multiply perforated plastic sheet as the nonwoven fabric.

FIG. 9 shows a construction of a dressing 70 having a fabric 72 formed of a sheet 74 of plastic having numerous apertures 76 extending through the sheet 74. The sheet 74 is elastomeric and, with the apertures 76, has physical characteristics similar to those of the fabric 32 of the dressing 20 in FIG. 2. In FIG. 9, the fabric 72 is bonded to the film 24 in the same fashion as has been described above for the bonding of the fabric 32 to the film 24. There follows an analysis of the dressing 20 which is understood to apply also to the dressing 70.

It is noted that the nonwoven material of the fabric layer 32 has sufficient elasticity to permit abrasion by a pointed object, such as a hair pin 66, as shown in FIG. 8. The fabric layer 32 distorts under stress of the hair pin 66 while distributing stress lines 68 about a region of the film 24 which is substantially larger than the region of contact of the hair pin 66 with the fabric layer 32. In the preferred construction of the dressing 20, the nonwoven material of the fabric layer 32 is spun-bonded. Spun-bonded material has a substantially larger capacity to absorb deformation from an abrading object than does the film 24. Thus, an abrading object which might well tear the film 24 is kept away from the film 24 by the fabric layer 32. Thereby, the film 24 is protected by the fabric so as to maintain integrity of the barrier against infection from bacteria. It is further noted that the distribution of the stress lines 68 about the relatively large area of the film 24 allows the film 24 to serve as a strong base for support of the fabric layer 32 in resisting the force of abrasion without any danger of tearing the film 24.

The film 24 may be of the form described hereinabove, which form is constructed of a water vapor permeable polyurethane or acrylate copolymer, or urethane and urethane copolymers as well as modified polypropylene, which film is transparent and has sufficient elasticity to be conformable to contours of a human body as well as an animal body. Typically, the film 24 has a thickness in a range of approximately 1–3 mils, though film thicknesses in the order of 0.5–10 mils may be considered. The thickness of the film in combination with the amount of voids in the plastic material of the film determine a transport rate for water vapor through the film. A transport rate greater than approximately 250 grams per square meter per 24 hour interval at a relative humidity of 80% is desired in order to insure that the skin of a patient wearing the dressing 20 can breathe properly in the sense that water vapor discharged through the skin can permeate through the film 24 to be evaporated in air. Test conditions for the vapor transport rate is in accordance with a standard condition set forth in ASTM E96 Condition BW. Further details in the construction of a moisture vapor transmitting elastomeric film is disclosed in Metcalfe et al, U.S. Pat. No. 4,596,738 issued Jun. 24, 1986. Further details in the construction of a moisture-vapor-permeable pressure-sensitive adhesive material is disclosed in Hodgson, U.S. Pat. No. 3,645,835 issued Feb. 29, 1972 and reissued as U.S. Pat. No. Re. 31,886, on May 14, 1985.

The nonwoven material of the fabric 32 is particularly advantageous over woven material because the nonwoven material can be constructed in a form which is exceedingly thin for a protective layer, typical thicknesses of the fabric layer 32 being in the range of approximately 1–30 mils, with a typical value being approximately 10 mils. The nature of the spun-bonding construction introduces a low density to the spun-bonded material, much lower than a solid form of the material, such that there are adequate voids to allow for the evaporation of water vapor from the surface of the film 24. In addition, such material has a relatively soft fluffy feel which, in combination with the great elasticity, provides for the above-noted capacity to absorb stress of an abrading object, thereby to provide for the protection of the film 24.

It is noted that spun-bonded material is employed in the practice of the invention while woven fabric is not employed. This is because available woven fabric does not have the combination of thinness, elasticity, and air permeability of the spun-bonded material. Should these characteristics become available in woven fabric in the future, then such woven fabric may be employed in the practice of the invention as an alternate component to the spun-bonded material.

An alternative form of the fabric layer 32 employs a sheet of plastic having multiple perforations in a range of typically 25–50 mils, and wherein the combined area of the apertures is in the range of 5–30%, typically 17%, of the area of the plastic sheet. This is a highly discontinuous fabric providing ample opportunity for transpiration of water vapor. It is noted that the fabric is not waterproof in the sense that liquid water can pass through the fabric. However, the waterproof characteristic is not required of the fabric layer 32 because the film 24 provides an adequate barrier to the flow of water.

The spun-bonded material is formed by a fusing or by a chemical interaction of filaments of material in a random pattern rather than by weaving or knitting strands of material, as in knitted fabric. By way of example, spun-bonded urethane is a thermal plastic polyurethane elastomer formed as a spun-bonded fabric. The fabric has a structure of three dimensional entanglement of polyurethane fine continuous or discontinuous elastic filaments which are thermally or chemically melt bonded. The fabric is characterized by being stretchable in all directions, typically in excess of two times the relaxed length. The fabric is highly permeable to air because of the thinness of the fine filament structure, the filaments of the structure being randomly webbed and bonded only at their intersections to define interstices. The thickness of the fabric is in a range of typically 0.05–0.75 millimeters. The density of the fabric is in a range of typically 15–250 grams per square meter.

The second and the third adhesive layers 34 and 44 are solvent-based acrylic aerated adhesive layer having a thickness on the order of one mil. Permeability to water vapor may be increased by flash heating to sputter out the solvent vehicle which carries the adhesive particles, the sputtering leaving voids in the adhesive which facilitate transport of water vapor through a layer of the adhesive.

The release coat, applied to the upper surface of the film 24, and the release coat applied to the upper surface of the fabric layer 32 are formed, preferably, as a silicone-based coating. If desired, the coating may be fused to the underlying substrate of film 24 or layer 32 by heat. Such release coats may be cured by bombardment with an electron beam or by treatment with an ultraviolet beam.

In a further aspect of the invention, it has been found that the fabric layer 32, by itself, has sufficient tensile strength to be used as an elastic bandage for binding wounds, such as a sprained ankle, or other sprained joint. A spun-bonded material, such as a polyurethane spun-bonded material, is transmissive to sweat without absorbing the sweat. Increased comfort to a person wearing the elastic bandage is attained by providing material which absorbs the sweat. This is accomplished, in accordance with another aspect of the invention by applying a sweat-absorbent material such as cotton or rayon particles by a flocking of the particles on the spun-bonded material. The flocking process comprises a spraying of both an adhesive and the particles of cotton or rayon on the spun-bonded material, the adhesive securing the flocked particles on the spun-bonded material. Sufficient comfort is provided to the wearer of the bandage by flocking only the side of the bandage which faces the skin of the wearer. A layer of absorbent material can also be provided by use of powdered hydrophilic foam prepared as a slurry in the adhesive and deposited on the nonwoven material. Also, if desired, the cartoon characters can be imprinted on the material of the elastic bandage. Also, the printing of other indicia on the elastic bandage can be accomplished in a compressed format such that, upon a stretching of the bandage during a binding of a wound, the indicia expand to the desired proportions to indicate a proper amount of tension in the elastic bandage.

The use of nonwoven material is, furthermore, distinctly advantageous over the use of woven material because the nonwoven material can be constructed as a much thinner sheet which allows flexing of the film 24 without introduction of unnecessary stress as might occur when a thin film of material is bent around a thick layer of material, as would occur if woven material were used as the protective layer. By use of two very thin layers, each having a thickness on the order of one mil as is the case with the disclosed film 24 and fabric layer 32, the resultant dressing has the flexibility and conformability of the layer of skin which is covered by the dressing 20. By considering this conformability characteristic in combination with the capability to breathe, to resist liquid water, and to exclude infectious agents, the dressing 20 may well be regarded as a synthetic skin. It is also noted that, in view of the secure adhesive bond between the film 24 and the skin 28 of the patient, the film and skin can be regarded as a composite structure which serves as a foundation for support of the protective layer 32 of fabric. This is an important part of the protective mechanism which, as noted above with reference to FIG. 8, provides that the protective layer deforms more readily in response to an abrasive force than does the composite structure of the film and the skin. There results the distribution of the abrasive forces about the composite structure of the film and skin to reduce the magnitude of such force at any one point on the film, thereby to inhibit a tearing of the film. In this respect, the dressing 20 has a further characteristic of skin in that the fabric 32 may be likened to the epidermis which protects the dermis from abrasive forces.

Figure 10:
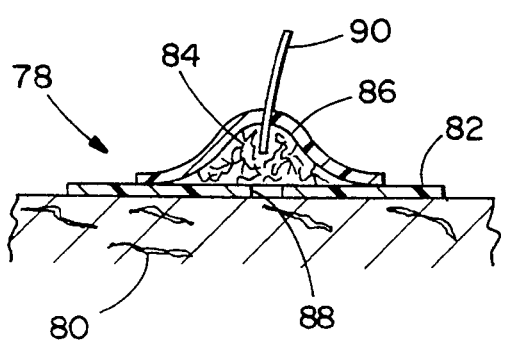
FIG. 10 shows a construction of an electrode suitable for adhesion to a human body for measurement of body functions, the electrode being formed of electrolyte absorbing material in combination with a layer of nonwoven material.

FIG. 10 shows the construction of a flexible electrode assembly 78 which is secured adhesively to the skin 80 of a patient, the electrode assembly 78 being formed of a layer 82 of nonwoven fabric such as the layer 32 of FIG. 2 so as to be moisture permeable and comfortable for wearing by the patient. A flexible sponge 84 or similar liquid absorbent material is enclosed by a flexible elastomeric cap 86 which is fused to the layer 82 for securely holding the sponge 84 in place. The cap 86 may be formed of the same material as the layer 82. An aperture 88 is disposed within the layer 82, and centered beneath the sponge 84. An electrode wire 90 passes through the cap 86 to make contact with the sponge 84, the wire 90 being secured to the cap 86 by fusing of the cap material about the wire 90.

In operation, the sponge 84 contains a gel of electrolyte which provides an electrically conductive path between the wire 90 to the skin 80, the electrolyte making contact with the skin 80 via the aperture 88. The elastomeric properties of the nonwoven material of the layer 82 and of the cap 86, wherein recoverable stretch may be as much as 100% in three dimensions allows the electrode assembly 78 to conform to undulations in the skin 80 and to distend with movements of the patient. This permits a much more secure holding of the electrode assembly 78 to the skin 80 of the patient. In addition, the moisture-permeable and air-breathable qualities of nonwoven fabric, particularly spun-bonded fabric, in combination with the extreme thinness of the fabric insure comfort in the wearing of the electrode 78. The wire 90 is readily connected to electronic measurement circuitry for use in patient monitoring situations such as an electrocardiogram, transcutaneous nerve stimulation, and an electromylogram.

Figure 11:
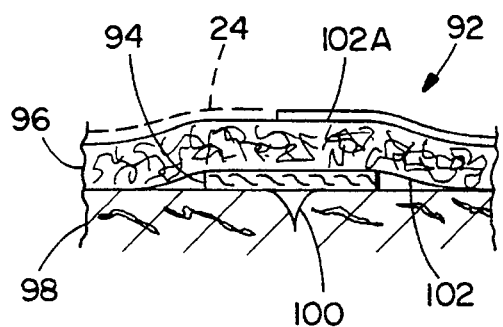
FIG. 11 shows a sectional view of a bandage structure in which nonwoven fabric secures a gauze pad to skin.

FIG. 11 shows a simplified form of bandage 92 in which a gauze pad 94 is secured by a layer 96 of spun-bonded fabric to the surface of skin 98, which skin may be the skin of a human or an animal. The gauze pad 94 serves to absorb exudate from a wound 100 in the skin 98 and to protect the wound 100 from an external environment. The gauze pad 94 is permeable to both water vapor and to air. The layer 96 is secured by an adhesive 102 to the surface of the skin 98, the adhesive 102 being disposed along the bottom surface of the layer 94. The adhesive 102 also serves to secure the pad 94 to the layer 96. The spun-bonded fabric of the layer 96 is elastomeric with three dimensional stretch, them being recoverable stretch in excess of 100% along each of the three dimensions. Open regions of the spun-bonded fabric occupy at least 30% of the total surface area of the layer 96. Thickness of the layer 96 is in the range of 0.05 to 0.75 millimeters. These characteristics of the spun-bonded fabric give the layer 96 the capacity to conform to undulations of the skin 98, including a stretching of the skin in the situation wherein the skin covers a limb which is being bent such as at a knee or elbow. In addition, the open spaces or voids within the fabric provides sufficient air permeability for increased comfort to the person wearing the bandage. Since the bandage 92 does not include the film 24 of FIG. 2, the bandage 92 of FIG. 11 is to be employed only in those situations, such as mild skin irritations and/or mild wounds in which external moisture is not a hazard, and wherein the amount of exudate from the wound 100 is sufficiently small so as to be totally absorbed by the pad 94.

With reference now to FIGS. 12, 13, and 14, there is shown a dressing 104 comprising a film 24 and a layer 32 of nonwoven fabric as was disclosed in the construction of the dressing 20 of FIG. 2. The drawing of FIGS. 12–14 has been simplified in that the mode of bonding the film 24 to the nonwoven layer 32 is not shown, it being understood that any of the above-disclosed methods such as fusing, or adhesive with or without the release coat may be employed. The adhesive layer 26 is disposed along a surface of the film 24 for securing the film 24 to the skin of a patient. However, instead of the release sheet 30 disclosed in the dressing 20 of FIG. 2, the dressing 104 of FIGS. 12–14 employs a release sheet 106 which is composed of two sections, namely, a first section 106A and a second section 106B.

In accordance with a feature of the invention, the first section 106A of the release sheet has two folds, namely, a first fold 108 and a second fold 110, the two folds 108 and 110 dividing the first section 106A of the release sheet into three panels, namely a first panel 112A, a second panel 112B, and a third panel 112C. The fold 108 joins the panels 112A and 112B. The fold 110 joins the panels 112B and 112C. The second fold 110 is in a reverse direction to the direction of the first fold 108 to direct the third panel 112C across the adhesive layer 26 to rest upon the second section 106B of the release sheet 106. The arrangement of the two folds 108 and 110 wherein one fold is directed in reverse direction of the other fold constitutes a fold assembly which may be referred to hereinafter as a reverse fold. The second section 106B of the release sheet comprises a single fold 114 which divides a second section 106B into two panels, namely, a first panel 116A and a second panel 116B.

The view of the dressing 104 of FIGS. 12 and 13 is shown in the upside-down orientation relative to the presentation of the dressing 20 in FIG. 2. The reversed presentation of the dressing 104 is employed to reflect the orientation of the dressing 104 prior to application of the dressing to the patient. Prior to application of the dressing 104 to the patient, the dressing 104 is grasped by a nurse or physician with the right-hand side of the dressing 104 including the second section 106B of the release sheet being held, typically, in the right hand of the nurse or physician. The dressing 104 is thus supported in cantilevered fashion with the result that the dressing 104 flexes to draw an outer end 118 away from the second panel 116B of the second section 106B of the release sheet. Then the nurse or physician grasps the outer end 118 with the left hand and pulls the third panel 112C away from the adhesive layer 26 as shown in FIG. 12 to expose a central region of the adhesive layer 26. The central region of the adhesive layer 26 is sufficiently large to allow the nurse or physician to apply the dressing 104 to the skin of the patient. Accordingly, the next step in the application of the dressing 104 is the emplacement of the central section of the film 24 with the adhesive layer 26 therein upon the wound 50 (FIG. 2) of the patient. Thereafter, the third panel 112C is pulled completely away from the film 24 to allow securing of the left end of the dressing 104 to the patient. This is followed by a grasping of the second panel 116B on the right side of the dressing 104, and a pulling away of the second section 106B of the release sheet 106 to secure the right end of the dressing 104 to the patient.

A particular advantage provided by the reverse fold is the fact that the adhesive layer 26 presents a slight force of adhesion to the third panel 112C, which force is overcome by the nurse or physician on drawing the third panel 112C away from the film 24. However, it should be noted that there is no adhesive force at the interface (FIG. 13) between the second panel 112B and the third panel 112C. Therefore, as the nurse or physician draws the third panel 112C away from the film 24, there is a sudden termination of the adhesive force as the third panel 112C clears the location of the first fold 108. The resulting "snap-action" is immediately felt by the nurse or physician and signifies that the dressing 104 is now ready to be applied to the patient. Thus, the nurse or physician need not continuously watch the dressing 104 as the third panel 112C is withdrawn, but may keep his or her eyes on the patient during the withdrawal of the third panel 112C and during application of the dressing 104 to the patient.

The material used in construction of the release sheet 106 is flexible and may be the same as that employed in the construction of the release sheet 30 (FIG. 2). For example, the release sheet 106 may be made of a flexible material employing a paper base or a plastic base. The selection of material is a matter of convenience in use and in manufacture of the release sheet. It is also noted that the construction of this embodiment of the invention may be varied such that the outer end 118 of the third panel 112C may extend partway along the top surface about the second panel 116B as shown in solid lines in FIG. 13 or, alternatively, may be elongated as shown in phantom at 118A to extend beyond the end of the second panel 116B at the right side of the dressing 104. The choice of the outer end 118 or the elongated outer end 118A is simply a matter of convenience in the use of the dressing 104.

FIG. 15 shows a dressing 104 which is a modification of that disclosed in FIGS. 12–14, the modification being that the second section 106B of FIG. 12 is replaced in the modification of FIG. 15 with a second section 106B' of release sheet having the first-mentioned fold 114 plus two additional folds, namely, a second fold 120 and a third fold 122. In FIG. 15, panels and sections of the release sheet which correspond to the panels and sections of the release sheet of FIG. 12 are provided with the same identifying numerals except that, in FIG. 15, the corresponding panels and sections are further identified by a prime sign following the identifying numerals. In FIG. 15, the three folds 114, 120, and 122 divide the second section 106B' of the release sheet 106' into four panels, namely, the first panel 116A', the second panel 116B' a third panel 116C, and a fourth panel 116D. The fold 120 separates the second panel 116B' and the third panel 116C. The third fold 122 separates the third panel 116C and the fourth panel 116D. It is noted that the assembly of the first fold 114 and the second fold 120 constitute a reverse fold operative in the same fashion as the reverse fold of the first sheet section 106A disclosed in FIG. 12. In FIG. 15, the first section 106A' of the release sheet is configured in the same fashion as the first sheet section 106A of FIG. 12, the first sheet section 106A' of FIG. 15 comprising three panels 112A', 112B' and 112C' which are joined by the folds 108 and 110. In the folded configuration of the dressing 104', the outer end 118 of the third panel 112C' rests upon the fourth panel 116D of the second sheet section 106B'.

The operation of the release sheet of FIG. 15 is similar to that disclosed for the release sheet of FIGS. 12–14. However, the configuration of release sheet of FIG. 15 is more convenient for large dressings because the additional third panel 116C is provided to cooperate with the third panel 112C' to cover the central section of the adhesive layer 26. In the case of larger dressings, it may be inconvenient to have a single large flap of release sheet, such as the panel 112C of FIG. 12, to cover the entire central region of the adhesive layer 26 and of the film 24. By providing two flaps of release sheet, namely, the third panel 112C' and the third panel 116C of FIG. 15, each of the flaps of release sheet can have a size which is convenient to manipulate by the nurse or physician applying the dressing to a patient. During the process of applying the dressing 104' to the patient, the nurse or physician first grabs the outer end 118 of the third panel 112C' to withdraw this panel from the adhesive layer 26. This is accomplished with the above-noted snap-action. Then, the nurse or physician grasps the fourth panel 116D of the second section 106B' of the release sheet, and proceeds to withdraw the third panel 116C from the adhesive layer 26. The withdrawal of the third panel 116C is also accomplished with the snap action due to the presence of the reverse fold in the second section 106B' of the release sheet.

With respect to the extent of the outer end 118 of the third panel 112C', it is noted that the outer end 118 may lie upon the top surface of the fourth panel 116D and extend partway across the fourth panel 116D (FIG. 15) in the manner disclosed above (FIG. 13) wherein the outer end 118 lies upon the second panel 116B. Alternatively, if desired, the outer end 118 of the third panel 112C' may be extended to lie beyond the end of the fourth panel 116D in the folded or closed configuration of the dressing 104' in a manner analogous to that disclosed in FIG. 13 with reference to the extended outer end 118A. Again, the choice of length to the outer end 118 is a matter of convenience to the person utilizing the dressing 104'.

A further advantage of the folded configurations of release sheet of FIGS. 12–15 is the fact that the panels of the release sheet serve to stiffen the dressing when the release sheet is folded, for example as shown in FIG. 13, for storage of the dressing and for handling the dressing prior to application of the dressing to a patient. The stiffening of the dressing facilitates manipulation of the dressing by a nurse or physician prior to application of the dressing to the patient. The stiffening is sufficient such that, even in the absence of the layer 32 of nonwoven fabric, the remaining assembly of film and release sheet are still readily manipulated without danger of entangling the film 24. During a process of application of such a dressing consisting of the film 24 without the fabric layer 32, the snap-action provided by the reverse fold during withdrawal of a flap of the release sheet enables a nurse or physician to maintain sufficient tension in the film so that the film can be applied to the patient without danger of entanglement, creasing, or folding of the film 24. Therefore, the configurations of folded release sheet disclosed in FIGS. 12–15 enable the application of the film itself to the patient. If desired, a layer of nonwoven fabric can be secured subsequently to an outer surface of the film by use of an adhesive layer, as was disclosed with reference to FIG. 2.

FIG. 16 shows a dressing 124 which is an alternative embodiment to the dressing 20 of FIG. 2. The dressing 124 comprises the film 24 and the layer 32 of nonwoven fabric as was disclosed in the construction of the dressing 20 of FIG. 2. However, the construction of the dressing 124 differs from the construction of the dressing 20 with respect to the manner of forming the adhesive layers. In FIG. 16, the dressing 24 is secured to the skin 28 of the patient by a first adhesive layer 26A which is formed with an array of windows or perforations 126 which may be located in rows and columns or as a random array of perforations. The fabric layer 32 is secured to the film 24, in FIG. 16, by a second adhesive layer 34A comprising an array of islands 128 of adhesive. The islands 128 may be arranged in a regular array of rows and columns, or may be arranged in random fashion. The arrangements of adhesive in the layers 34A and 26A am the inverse of each other in the sense that the perforations of the layer 26A becomes the islands in the layer 34A.

For the securing of the fabric layer 32 to the film 24, either configuration of adhesive may be employed, namely the configuration with the islands 28, or the configuration with the perforations 126. It is noted that in the adhesive layer 34A, the islands are spaced apart from each other, and that in the adhesive layer 26A, the perforations 126 are spaced apart from each other. For the securing of the film 24 to the skin 28, only the adhesive configuration of the perforations 126 of the adhesive layer 26A should be employed in order to insure that there is no migration of bacteria, or other source of infection, along the interface between the skin 28 and the dressing 124. In the case of the array of islands 128 of adhesive, as shown in the layer 34A, such migration of bacteria or other source of infection may be possible by passage between the islands 128 of adhesive.

The adhesive layers 26A and 34A of FIG. 16 offer the following advantage over the corresponding layers 26 and 34 of FIG. 2. In FIG. 16, the adhesive layers provide for a greater capacity of the dressing to breathe by virtue of the open spaces in the adhesive layers. Indeed, by using a sufficient amount of open spacing in both of the adhesive layers 34A and 26A, it is possible to use adhesive material which is non-breathable, adequate capacity for breathing being provided to the dressing 124 by virtue of the open spaces provided by the perforations 126 and by the spaces which surround each of the islands 128. If desired, the islands 128 can be made of varying sizes and shapes and, similarly, the perforations 126 can be made with varying sizes and shapes. Typical shapes would be squares or circles, the latter being shown in FIG. 16.

In the construction of the adhesive layers 34A and 26A, it is noted that these layers may be deposited in the film 24 by a process of printing or screening. In the case of the layer 26A, and with a breathable adhesive material, a typical range of open space provided by the array of perforation 126 is in the range of 10%–40% of the total area of the adhesive layer. In the case of a nonbreathable adhesive material employed in the construction of the layer 26A, a typical range of dimension for a window or perforation 126, assuming square perforations, would be a range of approximately 0.1 millimeter to 4 millimeters on a side of a square. It is possible that a minimal size of square can be as small as 0.03 millimeters. If desired, a large central window, substantially larger than the perforations 126 could be employed if it is desired to avoid any adhesive in a central portion of the dressing. In the case of a nonbreathable adhesive, the perforations 126 of the layer 26A should have a spacing less than approximately one millimeter. In the case of the islands 128 of layer 34A, the total area of adhesive of the islands 128 may be in a range of approximately 10%–40% of the total layer area.

It is to be understood that the foregoing ranges of window and island areas are given by way of example for typical constructions of dressing, and that the foregoing dimensions and amounts may be varied from those disclosed if necessary for a specific application. By way of example, the use of the islands 128 reduces the total adhesive force between the fabric layer 32 and the film 24 so as to facilitate a peeling of the fabric layer 32 away from the film 24 as may be done for a viewing of a wound in the patient. Greater adhesive strength is provided by enlarging the diameters of the islands 128 while a reduction in adhesive strength is provided by decreasing the diameters of the islands 128. Also, the adhesive force can be increased by placing the islands 128 closer together and reduced by placing the islands 128 further apart. It is believed that the diameters of the islands 128 should be at least as large as the diameters of filaments in the fabric layer 32 so as to insure good adhesion.

It is to be noted that the use of the configuration of islands 128 of adhesive can facilitate the releasing of the fabric layer 32 from the film 24 to such an extent that a release coat, such as the release coat 26 of FIG. 2, is not required. This is particularly advantageous from a manufacturing point of view in that the manufacturing process is simplified. Also, the elimination of the release coat provides still further opportunity for increasing the capacity to breathe.

FIG. 17 shows a plurality of dressing sections 130 secured one upon the other to form a composite dressing 132. The dressing 132 is secured to the skin of a patient by a layer of adhesive 134. Each dressing section 130 comprises a nonwoven fabric layer 32 bonded to a film 24 as has been disclosed with reference to FIG. 2. In FIG. 17, the bonding between a fabric layer 32 and a film 24 in any one of the sections 130 is accomplished by any of the methods disclosed hereinabove, including fusing, the use of an adhesive layer with or without a release coating, a perforated layer such as the layer 26A of FIG. 16, or an array of adhesive islands as the layer 34A of FIG. 16. An adhesive layer 136 is employed for securing the top one of the sections 130 to the middle section 130, and an adhesive layer 138 is employed for securing the middle section 130 to the bottom section 130. For ease of manufacture, the adhesive layers 136 and 138 may be fabricated as the layer 34A of FIG. 16 so as to avoid the necessity for providing a release coating. If desired, the layers 136 and 138 can each be replaced with a composite of two layers as disclosed in FIG. 2, namely the layer of adhesive 34 in conjunction with the layer of release coat 36. The adhesive strength of the layer 138 is less than that of the layer 134. The adhesive strength of the layer 136 is less than that of the layer 138. This permits successive ones of the dressing sections 130 to be peeled off, one at a time, to provide a desired amount Of breathing capacity to the composite dressing 132.

In the construction of the composite dressing 132, the bottom adhesive layer 134 may be fabricated in the same fashion as the bottom adhesive layer 26 of FIG. 2 or, alternatively, may be fabricated as the layer 26A of FIG. 16. The nonwoven fabric layers 32 may be structured of the same constituent filaments, or may be constructed of different filaments. In particular, it is noted that any one of the fabric layers 32 may be constructed of elastic filaments which may be continuous or discontinuous, and which are bound together in accordance with any one of different manufacturing processes, currently available, with open spaces between the filaments to permit propagation of water vapor. The securing of filaments to contiguous filaments may be accomplished by fusing, melting, or possibly by adhesion. The individual filaments may vary in rigidity and resilience depending on the specific plastic material from which the filaments are fabricated, the diameters of the filaments, and the density of packing of the filaments within the fabric of a layer 32.

The dressing sections 130 may be fabricated with equal capacity for breathing or with unequal capacity for breathing as may be desired. In a typical configuration of the composite dressing 132, the bottom dressing section 130 contiguous the skin would provide the greatest resistance to vapor transport with the other two sections 130 providing relatively little resistance to vapor transport. In this way, the middle section 130, or both the middle and the top sections 130 may be added as necessary to finally adjust the rate of vapor transport from the skin 28 to the outer atmosphere. In addition, by peeling off the top or both the top and the middle sections 130 and by subsequent replacement of these sections 130, the rate of vapor transport can be varied with time to suit needs of the patient. It is also noted that the three sections 130 shown in FIG. 17 are provided by way of example, and that more sections 130 (not shown) may be added to the composite dressing 132 if desired.

FIGS. 18 and 19 show yet a further embodiment of the invention in which a dressing is provided which is permeable to water vapor but impermeable to liquid water. In embodiments of the invention described above, these properties were provided by the use of a film. The film was manipulated and protected from the environment by a layer of nonwoven fabric, as disclosed in FIG. 2, or at least manipulated by a release sheet as disclosed in the discussion of FIGS. 12–15. However, in the embodiments of FIGS. 18 and 19, the film is dispensed to provide that a very thin barrier to the flow of liquid water is formed within and upon a layer of nonwoven fabric. The barrier may be extremely thin, the thickness approaching the size of molecules of the polymer employed in constructing the barrier. The extreme thinness promotes vapor transport so as to make the dressing highly breathable.

As shown in FIG. 18, the composite product of nonwoven material plus vapor barrier may be constructed by bringing together two layers of nonwoven fabric 140 and 142 which are provided by sources 144 and 146, respectively, of the fabric. For example, the sources 144 and 146 may be reels of fabric which are unwound to provide the fabric. The fabric layer 140 is passed between a print roll 148 and an idler roll 150 to a site 152 where the two fabric layers 140 and 1 42 are to be joined together. The fabric layer 142 is guided from the source 146 around a drum 154 to the site 152. The print roll 148 and the drum 154 are rotated by means of a motorized drive which is well known, but is not shown, so as to simplify the drawing. A pressure roll 156 is located in alignment with the drum 154 but on the opposite side of the site 152 from the drum 154 so as to cooperate with the drum 154 in pressing together the fabric layers 140 and 142. A dispenser 158 sprays liquid polymer upon the print roll 148, which liquid polymer is to cure subsequently to form the barrier. A dispenser 160 sprays liquid adhesive on a surface of the fabric layer 142 for subsequently bonding together the two layers 140 and 142.

In operation, the barrier-forming liquid from the dispenser 158 is spread evenly about the print roll 148 to form a thin film of liquid about the cylindrical surface of the print roll 148. As the roll 148 rotates, the film of liquid is brought into contact with a surface of the fabric layer 140. In accordance with the rheology of the liquid in contact with filaments of the fabric, (See also FIG. 19.), hydrostatic forces draw the liquid onto and between sections of filament, the liquid subsequently curing to form the barrier as indicated by a dashed line 162. The material of which the barrier 162 is formed may be the same material employed in constructing the film 24 of FIG. 2. However, as may be noted from FIG. 19, the thickness of the barrier can be on the same order of magnitude as the wall thickness of a soap bubble. This is very much thinner than the film 24 which must have sufficient strength to undergo mechanical processes such as being rolled on a roller and fed through mechanical apparatus employed in the construction of dressings.

In FIG. 18, the construction process continues by bringing the adhesively coated surface of the fabric layer 142 into contact with the surface of the fabric layer 140 to which the barrier liquid has been applied. The two layers are pressed together lightly by the roll 156 and the drum 154 to adhesively secure the layer 140 to the layer 142. This produces a laminated product of nonwoven breathable material. if desired, the adhesive may be sputtered on irregularly to provide wide open spaces for increased breathability. Also, in lieu of adhesive, a hot wire or other means can be employed at the site 152 for fusing together the layers 140 and 142.

The use of the second fabric layer 142 contiguous to the fabric layer 140 contained in the barrier 162 provides for protection of the barrier 162, to the extent that portions of the barrier 162 may be formed along the exterior surface of the fabric layer 140. However, even in the absence of the second fabric layer 142, the first fabric layer 140 with the barrier 162 formed therein serves well as a dressing wherein the barrier 162 is highly permeable to water vapor while being impermeable to liquid water. The nonwoven material of the layer 140 provides protection to the barrier 162, and also facilitates manipulation of the barrier 162 so that it can be placed, as part of a dressing, upon the skin of a patient.

The composite structure of the layer 140 of nonwoven fabric with the internal barrier 162 may be referred to hereinafter as a barrier assembly 164. For use of the assembly 164 as a surgical dressing or covering, it may be desirable to apply the barrier assembly 164 to the patient without adhesive layer (such as the layer 26 of FIG. 2) but with adhesive tape located at a periphery of the barrier assembly 164. Such would be the situation in which the barrier assembly 164 is to be employed for covering a severe burn in which the skin has been destroyed. In such situations, there is no substrate upon which the adhesive can attach and, furthermore, the adhesive may interfere with healing. The surface 166 of the layer 140 to which the barrier liquid has been applied by the prim roll 148 would contact the site of the burn wound for containing body liquids within the patient.

The barrier assembly 164 may also be employed in conjunction with the second fabric layer 142 as a laminated product to serve as a cover 168. The laminated cover 168 provides the foregoing features of vapor transport while being impermeable to liquid water. However, the cover 168 can be used in a wide variety of situations other than that of a surgical dressing. For example, by placing the surface 170 in contact with a wet surface, or a surface from which water exudes, the fabric layer 142 has the opportunity to absorb the excess water while the barrier 162 contains the water within the cover 168. In this situation, it may be advantageous to employ a nonwoven hydrophilic material such as a hydrophilic foam in the construction of the layer 142 or 140.

For example, an ideal situation for use of the cover 168 is in the construction of a baby's diaper for containing urine excreted by the baby. In such a case, the fabric layer 142 would be made much thicker than in the case wherein the cover 168 is to be employed as a surgical dressing. In the case of the surgical dressing, the laminated cover 168 may be employed with either the surface 170 or the opposite surface 172 in contact with a person's skin. However, in the case of the diaper, the surface 170 of the cover 168 would contact the baby's skin. Indeed, the cover 168 may be used in other applications requiring impermeability to water, such as in the construction of a garment, particularly a raincoat. In the construction of outdoor garments, such as a raincoat or a ski suit, it may suffice to employ only the layer 140 with the barrier 162 on the outer surface of the garment to shed water, in which case the layer 142 would not be used. If desired, the layer of barrier material can be deposited to a greater thickness by the roll 148 so as to produce an outer surface in the form of the film 24 (FIG. 2), but possibly with greater thickness for increased resistance to abrasion. In the resultant composite material of film and nonwoven components, there is a layer of film on a surface of the nonwoven fabric, and wherein portions of the film extend into interstices of the nonwoven fabric for improved adhesion to the nonwoven fabric. For example, the extension into the nonwoven fabric might be ten percent of the thickness of the nonwoven fabric in the case of a garment. The requisite elasticity for both the nonwoven fabric and the film may be reduced in the case of a garment from that required of a dressing located at a joint in a persons's limb because of the mobility of a freely fitted garment about a wearer of the garment. It is noted also that the barrier assembly 164 may be employed as a section 130 (FIG. 17) of the composite dressing 132.

In the construction of the cover 168 of FIGS. 18 and 19, as well as in the construction of the dressing 20 of FIG. 2, as well as the dressing portrayed in other ones of the figures, it is advantageous to employ the same type of plastic material in the filamentary fabric and in the film. The advantage is in better fusion between the film and the filaments of the nonwoven fabric. The film can fuse to the filaments in similar fashion to fusion of filament to filament in construction of the nonwoven fabric. The fusing may involve cross-linking of the plastic material. For example, the film or barrier may be constructed of a polyether polyester resin such as that provided commercially by DuPont under the name Hytrel, and the nonwoven elastomeric fabric may be constructed also of a polyether polyester resin in a fabric such as the fabric provided commercially under the name of Domique by Kimberly Clark. Polyurethane is also being employed for construction of nonwoven fabrics, as well as for film, this presenting a further opportunity for use of the same chemistry in construction of both the nonwoven fabric and the film. It is noted also that other techniques are becoming available for construction of the nonwoven filamentary material, for example, melt bond in addition to spun bond. in all cases the filaments are connected by some form of fusion, as distinguished from use of adhesives.

FIG. 20 shows a dressing 174 which is a further embodiment of the invention adapted for aseptic topical delivery of medication to a patient. The dressing 174 comprises a hydrophilic pad 176, a hydrophilic filter membrane 178 which is disposed on a top surface of the pad 176 and covers all or substantially all of the top surface of the pad 176, and a support 180 which holds the pad 176 against the skin 28 of the patient. The support 180 comprises a breathable film, a suitable film being the film 24 of FIG. 2. To facilitate manipulation of the film 24 during application of the dressing 174 to the patient, it may be advantageous to include a breathable stiffening element in the support 180, such as the layer 32 of nonwoven fabric disclosed in FIG. 2. The fabric layer 32 is bonded to the film 24 by means disclosed hereinabove such as by fusing, or adhesive (not shown in FIG. 20). By way of example, an adhesive layer 182 is shown for securing the film 24 and the support 180 to a peripheral region of the pad 176 and to a peripheral region of the membrane 178. However, if desired, another form of securing may be employed such as by welding, or by use of tape (not shown). An adhesive layer 184 secures the film 24 and the support 180 to the skin 28.

In accordance with a feature of the invention, the dressing 174 includes a window 186 which extends through the support 180 to receive medication. The medication is provided by a reservoir 188 which sits upon a ledge 190 of the window 186 and opens directly into the window 186.. An inlet port 192 of the reservoir 188 is closed off by a rubber stopper 194 which is readily pierced by the needle of a syringe 196 for injecting medication from the syringe 196 into the reservoir 188, thereby to fill the reservoir 188 with the medication.

In operation, the hydrophilic filter membrane 178 acts to admit a solution of medication while impeding the entry of bacteria, thereby to maintain a sterile field at the site of the wound 50 before, during, and after administration of the medication. The membrane 178 has a porosity which admits the medication, the porosity being measured by a pore size rating in the range of 0.2–0.22 microns, this being the nominal width of sinuous pathways through the membrane. The foregoing pore size rating does not allow propagation of bacteria or fungi along along the pathways, and thereby retains the sterile field. Suitable membranes are manufactured, by way of example, by Pall Corporation of Glen Cove, N.Y., by Millipore of Bedford, Mass., and by Gelman of Ann Arbor, Mich.

The support 180 may be fabricated also of the composite material of the barrier assembly 164 of FIG. 18 as well as a combination of a breathable film laminated with a breathable woven or nonwoven fabric. The film used in construction of the support 180 may be a microporous hydrophobic film material or a non-porous moisture vapor transmissible film. The film of the support 180 may be secured to the skin 28 by use of tape in lieu of the adhesive layer 184. The reservoir 188 may be fabricated of a rigid polycarbonate plastic, or a semirigid polyvinyl plastic, by way of example. The pad 176 may be fabricated of air-laid rayon fibers in the form of a nonwoven fabric as is employed in the common adhesive bandage. A fiber density of 2.65 ounces per square yard is suitable for fabrication of the pad 176. By way of further example, the pad 176 may be fabricated of surgical gauze or foam such as a urethane foam. The foam may be open-cell or closed-cell foam. A suitable hydrophilic foam is manufactured by W. R. Grace under the name of Hypol material. The pad 176 is hydrophilic so as to absorb the medication initially, and then allow the medication to mix slowly with body fluids as the medication enters the wound 50. The film 24 in cooperation with the reservoir 188 provides a liquid impermeable barrier which prevents egress of body fluids.

If desired, the reservoir 188 may be employed simply as a cover which would be removed to allow direct supply of medication to the membrane 178 and the pad 176 as by use of a dropper. In such case, it would be advantageous to replace the reservoir 188 with a cover (not shown in FIG. 20) of soft flexible material having the same outside dimensions of the reservoir 188, the composite material of the barrier assembly 164 being suitable. A further suitable cover for a window is shown by the window shade 40 (FIG. 2) covering the window 38 by use of an adhesive layer and a release coat, this arrangement being suitable for the window 186 of the dressing 174 (FIG. 20). The cover inhibits moisture vapor loss from the site of the wound 50.

FIG. 21 shows the dressing 20 of FIG. 2 with the release sheet 30 being placed with an imprinted release sheet 198. The release sheet 198 is imprinted with a topical reagent in the form of a repeating pattern of contours 200. The contours 200 are spaced apart so as to provide for a desired concentration of the reagent upon administering the reagent to a patient. By way of example, the topical reagent may be a drug, or medicine which can be administered through a person's skin. The release sheet 30 has no such reagent thereon and may be referred to as a plain release sheet.

FIGS. 22 and 23 taken together show the methodology of carrying out the feature of the invention wherein the dressing 20 serves the additional function of administering a topical reagent to the patient. FIG. 22 shows the printing of the topical reagent upon a surface of the release sheet 198, and the joining of the release sheet 198 to the film 24 by means of the adhesive layer 26. This is accomplished by the use of apparatus 202 comprising a drum 204 for paying out the sheet 198 and a drum 206 for paying out the film 24. Arrows on these drums indicate directions of rotation. The apparatus 202 further comprises a vat 208 which holds a solution 210 of the topical reagent and a textured print drum 212 which dips into the solution 210 and contacts the surface of the sheet 198 to print a pattern of a continuous coating of the reagent upon the surface of the sheet 198. By way of example, the surface of the drum 212 may be textured in the manner of the contours 200 (FIG. 21) so as to imprint the contour 200 upon the sheet 198. The drums 204, 206, and 212 are rotated by conventional means (not shown) so that the peripheral speed of the print drum 212 is equal to the speed of the sheet 198, and the speed of the sheet 198 is equal to the speed of the film 24.

Idler rolls 214 and 216 guide the sheet 198 to make contact with the print drum 212. Pressure rolls 218 and 220 urge the sheet and the film 24 towards each other to form a lamination 222 which may be cut subsequently into sections of suitable length to serve as a part of the dressing 20 (FIG. 2) or as a dressing 224 to be described in FIG. 23. Also included in the apparatus 202 is a dispenser 226 of adhesive, the dispenser 226 spraying adhesive into a surface of the film 24 to form the adhesive layer 26. The adhesive is sprayed by the dispenser 226 concurrently with movement of the film 24 so that the process of manufacture of the lamination 222 can be accomplished continuously. As the adhesive layer 26 passes between the pressure rollers 218 and 100, the adhesive forces interact to join the adhesive to the topical reagent to produce a resulting adhesive layer identified as layer 26A.

In FIG. 23, a portion of the lamination 222 is employed as a dressing 224, the dressing 224 being applied to the person's skin 28. Prior to application of the dressing 224 to the skin 28, the release coat 198 is peeled away from the adhesive layer 26A to expose the adhesive layer 26A to the skin 28. As the release sheet 198 is pulled away from the adhesive layer 26A, the adhesive forces of the adhesive upon the reagent are greater than the bonding forces of the reagent to the release sheet 198. This results in a separation of the reagent from the sheet 198 to form pockets 228 of the reagent at the surface of the layer 26A facing the skin 28. Assuming, by way of example, that the release sheet 198 has been imprinted with the contours 200 of FIG. 21, the locations of the pockets 228 correspond with the locations of the contours 200.

Upon application of the dressing 224 to the skin 28, the pockets 228 of the reagent are disposed at the interface between the adhesive layer 26A and the skin 28. The dressing 224 holds the reagent pockets 228 securely to the skin 228, even in the case of a bending of a limb as shown in FIGS. 1 and 5, so that the reagent can enter into the skin 28 and be dispensed thereby into the person's body. It is noted that the dispensing of the reagent takes place concurrently with other ones of the functions of the dressing 20, such as protection of skin and transport of water vapor as has been described hereinabove.

With reference to FIGS. 24–26, it is noted that a reagent can be printed on the release sheet 198 in a manner alternative to that of the periodic contours 200 (FIG. 110). In FIG. 24, a continuous coating of the reagent is imprinted along a central region 230 bounded by a margin 232 which is free of the reagent. By way of further example, in FIG. 25, the reagent is imprinted as a sequence of randomly distributed dots 234, each of the dots 234 being much smaller than the dressing 234. As a further example in the imprinting of the reagent upon the release sheet 198, FIG. 15 shows a series of stripes 236 of varying width and spacing in a regular pattern which does not repeat within the length of the dressing 224. The pattern of FIG. 26 provides for an increased concentration of the reagent in a central portion of the dressing 224, with reduced concentration of the reagent towards the ends of the dressing 224.

As noted above, FIGS. 22 and 23, taken together, provide the methodology of imprinting the reagent upon the release sheet 198, transferring the reagent to the adhesive layer 26 to provide the adhesive layer 26A, and then transferring pockets 228 of the reagent from the adhesive layer 26A to the skin 28. This procedure of the method may be modified to include the additional steps shown in FIG. 21 wherein the dressing 20 is initially formed with the plain release sheet 30 and then, subsequently, when it is desired to apply the reagent to the patient, the plain release sheet 30 is removed and is replaced with the imprinted release sheet 198. Thereby, upon application of the dressing 20 to the patient, the reagent can be dispensed topically. With respect to the gauze pad 48 (FIG. 2) employed with the dressing 20, the pad 20 would not normally be employed with the imprinted release sheet 198 unless it is desired to shield a selected portion of the person's skin from the reagent, in which case the pad 48 might be employed to provide this shielding.

By way of example, the dressing 224 (FIG. 23) may be formed of the following materials. The release sheet 198 may be a release paper such as that produced by the MEAD RELEASE PAPER COMPANY of West Chicago, Ill., the release paper being a siliconized paper such as Paper No. ST3A. Alternatively, a film coated with a release material such as a fluorinated hydrocarbon such as Teflon may be employed.

The printing process shown in FIG. 22 is a flexographic printing process; however, gravure or silk screen printing processes may also be employed. A suitable printing vehicle which enables the positioning of the topical reagent upon the release sheet is manufactured by COLORCON OF West Point, Pa. under the name of "NO-TOX". This is a clear varnish for narrow web flexographic printing, such as that provided under the part numbers VT-2010 or TF-6010. The drug, medicine, or active ingredient may be added alone to the varnish, or may be combined into a hydrophilic carrier prior to mixing with the varnish. The hydrophilic carrier is employed with a liquid active ingredient to place the ingredient in powder form, the powder form being suitable for mixing with the varnish. The drug may be a topical medication, antifungal medication, asteroid, or an antibiotic, by way of example. By way of further example, the active ingredient may be an antimicrobial such as provedine iodine.

The adhesive may be a solvent based acrylic adhesive such as that marketed by NATIONAL STARCH AND CHEMICAL COMPANY of Bridgewater, N.J. marketed under their Product No. 1054. Also, a solvent based acrylic pressure sensitive adhesive may be employed. It is to be understood that the foregoing types of release sheet, printing vehicle, topical reagent, and adhesive are provided by way of example, and that other suitable commercially available components may be employed in the practice of the invention.

If desired, the dressing 224 (FIG. 23) may be provided with a protective or stiffening layer 238, shown in phantom, to facilitate handling of the dressing 224. The layer 238 may be constructed as the fabric layer 32 (FIGS. 2, 7 and 8) of filamentary material or the fabric 72 (FIG. 9) of perforated film material or, if desired, a layer of super vapor-permeable film which is presently under development. There has been a steady improvement in the quality of vapor permeable films such that films now entering the manufacturing stage have a vapor transport rate many times higher than the 250 grams per square meter per 24 hour interval of time mentioned hereinabove. The term "super" is employed to differentiate between the newer higher-transport rates and the previous lower-transport rates. Due to the much higher vapor-transport rate, the layer 238 may be fabricated of the super permeable film, which film can be constructed of greater thickness than the film 24 while still allowing for an adequate vapor-transport rate for the dressing 224. This facilitates a handling of the dressing 224 by imparting greater rigidity to the dressing 224. Alternatively, if desired, the layer 238 may be releasably secured to the film 24 by use of the second adhesive layer 34 and the release coat 36 of FIG. 2 (not shown in FIG. 23). Also, if desired, the layer 238 may be formed in the manner of a border disposed over peripheral regions of the dressing 104, as shown by the border 52 of FIG. 3. If desired, the fabric layer 32 (FIG. 2) with the window 38 and the window shade 40 may be secured to the film 24 instead of the layer 238 in the dressing 104.

There have been further developments in the manufacture of elastomeric filamentary material with open spaces between the filaments suitable for the construction of the breathable fabric of the layer 32. If desired, the layer 32 may be structured of the same constituent filaments, or may be constructed of different filaments. The elastic filaments may be continuous or discontinuous, and are bound together in accordance with any one of different manufacturing processes, currently available, with open spaces between the filaments to permit propagation of water vapor. The securing of filaments to contiguous filaments may be accomplished by fusing, melting, or possibly by adhesion. The individual filaments may vary in rigidity and resilience depending on the specific plastic material from which the filaments are fabricated, the diameters of the filaments, and the density of packing of the filaments within the fabric of the layer 32. Generally, the fabric of the layer 32 has an open area greater than approximately 30% of the total surface area of the fabric layer.

The inventive feature of administering a topical reagent by use of the adhesive layer can be practiced with the layer 238 in any of the various forms of the layer 238, or without the layer 238. The protective or stiffening layer 238 has been shown in phantom because it is anticipated that thicker super permeable films will be available for construction of the film 24 in which case there may be adequate rigidity and resistance to abrasion in the film 24 without the need of the protective layer 238. In such a case, the dressing 224 may be employed without the layer 238, or may employ the layer 238 as an aid to packaging the dressing 224 for storing and marketing the dressing 104 prior to use. Also, instead of the layer 238, the dressing 224 can be constructed with any of the inventive features described in FIGS. 3–6.

It is noted also, with respect to the embodiment of the invention disclosed in FIG. 21, that the replacement of the plain release sheet 30 with the imprinted release sheet 198 offers the advantage in hospital use that only one form of completed dressing may need to be stored in a pharmacy, and that release sheets 198 imprinted with many different reagents may be stocked separately. This is particularly advantageous in the case of reagents which are used on an infrequent basis. In such case, a nurse or physician would simply peel off the release sheet 30 and replace the sheet 30 with the imprinted release sheet 78 having the desired reagent. The term "topical" as used herein includes any reagent which is to be applied to the skin or flesh of a patient, and includes reagents such as drugs, medicines, fungicides, antimicrobial agents, biologically active substances, and other materials including transdermal reagents which are to be applied topically.

The imprinting of the contours 200 of reagent on the release sheet 198 can be accomplished also with the release sheets 106 and 106' of FIGS. 12 and 15. By use of the release sheets, the reagent can be applied also to the dressing 124 of FIG. 16. and to the composite dressing 132 of FIG. 17. With respect to the composite material of FIGS. 18 and 19, the layer 140 of fabric with the barrier 162 can be substituted in many situations for the dressing 124 of FIG. 16 and the dressing 20 of FIG. 2. Therefore, in those situations, if desired, the reagent can be applied to the surface 166 of the layer 140 by means of the release sheet 198.

Also, with respect to the embodiment of FIG. 11, the bandage 92 can be formed with a layer of the film 24 located on the outer side, away from the skin, if desired, the film 24 covering all or part of the outer surface of the nonwoven layer 96. This would provide a smooth low friction surface to the bandage 92, so as to avoid rubbing against clothing as might occur with the relatively rough texture of the nonwoven layer 96. The film 24 would contain excess exudate from the skin 98. The layer of film 24 is readily secured to the layer 96 by an adhesive 102A of the same form as the adhesive 102.

In accordance with another aspect of the invention, the pad 48 of FIG. 2 provides both absorbency and a soft feeling to the touch which are beneficial to the healing process. While the pad 48 has been constructed of gauze in the embodiment of the invention of FIG. 2, other materials disclosed above such as a flocking of cotton, by way of example, may be employed in constructing the pad 48 for increased softness at the expense of reduced absorbency of body fluids. Such a situation would arise, for example, wherein it is desired to cover a large portion of the body with a covering of a laminated material comprising the film 24 and the nonwoven fabric layer 32 to provide the benefits of a body covering which allows for the transpiration of water vapor from the body. By way of example, the covering may be a drape or a garment. The flocking would provide increased comfort to the person wearing the covering. The flocking would extend to the edge of the film 24 and be secured by the first adhesive layer 26 to the film 24. Alternatively, if desired, the inverted arrangement of FIG.

11, wherein the film 24 is on the side of the fabric layer 96 away from the person's body, may be employed with the flocking being secured to the nonwoven fabric layer 96. This use of flocking may be accomplished with the bandage 92 of FIG. 11 by constructing the panel 94 of cotton flocking.

The properties of the covering for protecting the body of a person or an animal from the environment, while allowing for transpiration of water vapor, can also be obtained by substituting either the barrier assembly 164 of FIGS. 18 and 19, or the laminated product of the cover 168 (FIG. 18) in place of the laminated structure of the film 24 with the fabric layer 32 (FIG. 2) or the fabric layer 96 (FIG. 11). Flocking would be applied to either surface of the nonwoven material of the barrier assembly 164 or either surface of the laminated cover 168. By way of example, a layer 240 of flocking is shown applied to a top surface of the barrier assembly 164 opposite the surface 166 in FIG. 19.

Figure 27:
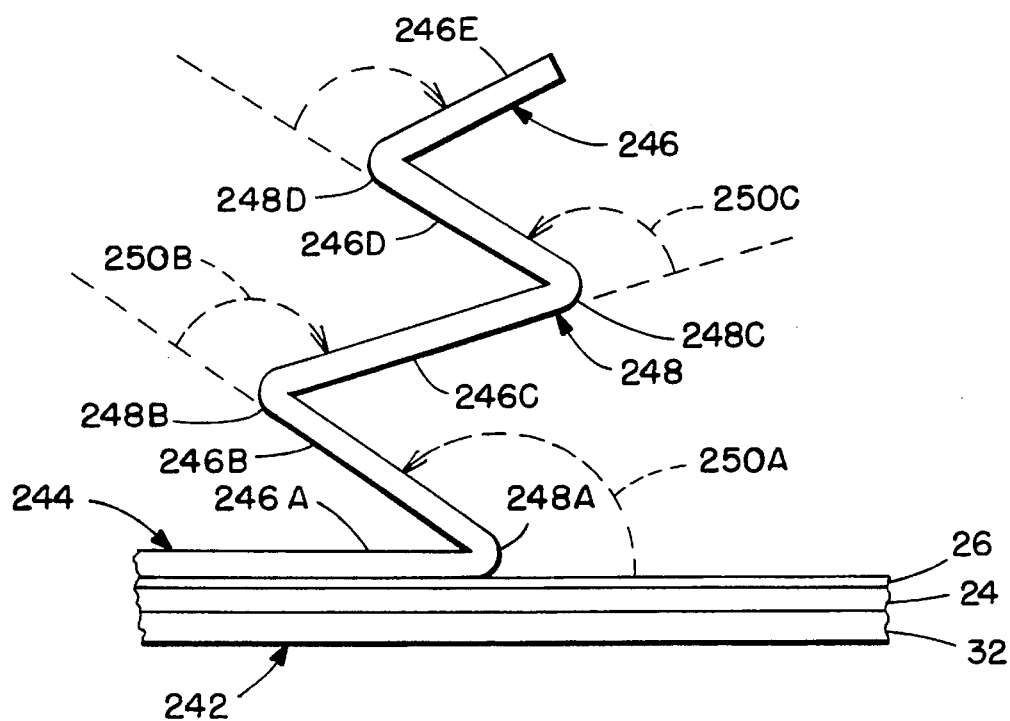
FIG. 27 shows a reversing fold sequence for a release sheet useful in explaining operation of the dressings of FIGS. 12–15.

FIG. 27 taken in conjunction with FIGS. 12–15 shows further details in the folding of the release sheet 106. In FIG. 27, there is shown a fragmentary view of a dressing 242 comprising the nonwoven fabric layer 32, the film 24 disposed upon the layer 32, the adhesive layer 26 disposed on the film 24, and a release sheet 244. By way of example, the release sheet 244 is folded in a plurality of panels 246 about a plurality of folds 248 wherein five panels 246A–E are shown folded about four folds 248A–D. Successive ones of the folds 248A–D are in opposite directions as are indicated by arrows 250A–D, respectively. Thus, the fold 248A is made by bending the release sheet 244 in the counterclockwise direction, and the fold 248B is made by bending the release sheet 244 in the clockwise direction. The panels 246 may differ in size, unlike an accordion fold wherein all panels are the same size. Accordingly, the arrangement of the folding of the panels 246 is referred to herein as a reversing fold sequence, and may have any number of panels 246 as may be convenient in the fabrication of the dressing 242. Similarly, in FIG. 15, the first and the second sections 106A' and 106B' of the release sheet 106' are folded each in a reversing fold sequence. A wound contacting region 252 is indicated in FIG. 13 to show independence of the folding and the locations of folds relative to the location of the wound contacting region 252. Also, in FIG. 15, a central portion 254 of the adhesive layer 26, located between the folds 108 and 114, is indicated to identify the portion of the adhesive layer 26 from which a section 106A' or 106B' of release sheet is to be peeled to attain a snap action.

Figure 28:
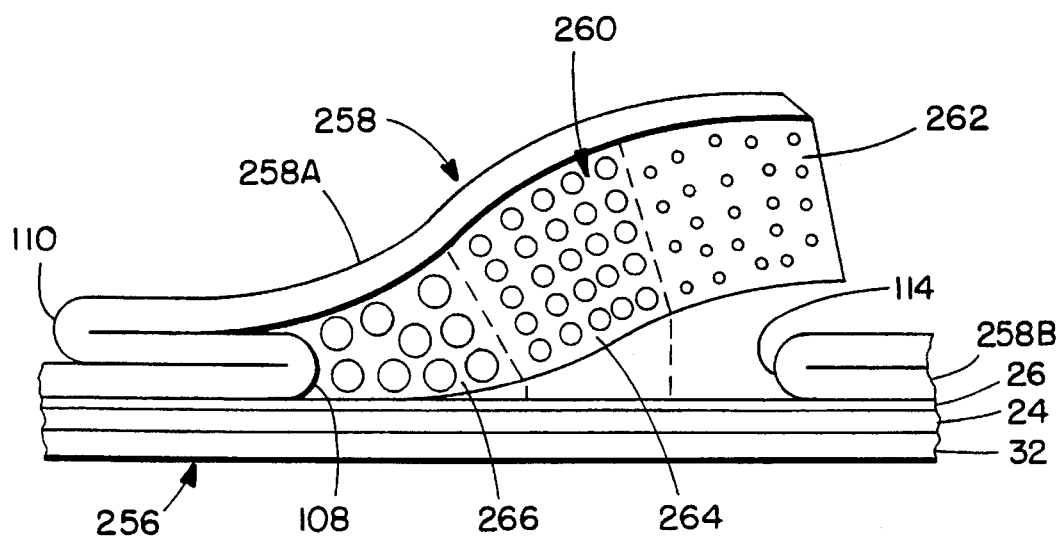
FIGS. 28 and 29 show, in stylized form, the production of a variable release force for a release sheet in the dressings of FIGS. 12–15.

FIG. 28 shows a dressing 256 which has the same construction as does the dressing 104 of FIG. 13, but furthermore includes a modified release sheet 258 comprising a first section 258A and a second section 258B wherein at least one of the release sheet sections 258A–B is provided with means 260 for varying the release force experienced during a withdrawal of the release sheet 258 from the adhesive layer 26. As is well known in the construction of release paper, the release force is dependent on the linear dimension of the separation line between the release sheet and the adhesive from which the sheet is to be separated, and is dependent also on the angle of attack between the release sheet and the adhesive layer during the separation process. Accordingly, the separation process is described in terms of a release value which is based on force per linear dimension of the separation line, and for a specific angle of attack. Release values are expressed by standardized tests such as the Instrom test or a test of the Pressure Sensitive Tape Council, PSTC #1 and PSTC #7. The release property of a release sheet, which may be a film, paper or fabric, is attained by coating the sheet with a well-known, commercially-available silicone material. Suitable silicone compounds may be water based or soluble in an other solvent to allow application of the material as a coating to the sheet by flexography or gravure printing methods. The coating may be attained also by dipping the sheet in a solution of the silicone material. The silicone material may be applied by use of a roller by equipment such as that portrayed in FIG. 18. The silicone coating may be cured by heat or ultraviolet radiation or by electron beam in accordance with well-known procedures.

In accordance with a feature of the invention, it is recognized that the release value and, hence, the release force experienced during a separation of the release sheet from the adhesive layer, can be altered by applying the coating to the release sheet in the form of pattern wherein the pattern is changed at different locations on the release sheet. For example, the pattern can be formed of little dots of coating wherein spacing and/or size of the dots can be altered from one location on the release sheet to another location on the release sheet. Alternatively, the pattern can be altered in terms of the extent or state of the curing of the silicone. FIG. 28 demonstrates this concept by the force varying means 260 which is constructed of sets of dots of release coating varying from a region 262 of widely spaced small dots to a region 264 of moderately spaced medium sized dots to a region 266 of closely spaced large dots. In the region 262 of the small dots, there is relatively little release material in the coating with the result that a relatively large force need be exerted to separate the release sheet 258 from the adhesive layer 26. In the region 264 of the medium dots, there is more release material in the coating with the result that a smaller force need be exerted to separate the release sheet 258 from the adhesive layer 26. In the region 266 of the large dots, there is substantially more release material in the coating with the result that a still smaller force is sufficient to separate the release sheet 258 from the adhesive layer 26.

Use of the release sheet 258 is advantageous in that the release force is reduced gradually over a plurality of stages of release coating pattern variations. Initially, a person separating the release sheet from the adhesive layer 26 experiences a relatively large force as the region 262 of small dots is withdrawn from the adhesive layer 26, this force abating in a prescribed fashion in the regions 264 and 266 of the medium dots and the larger dots prior to the snap action which occurs during the opening of the fold 110. Thereby, a user of the dressing 256 experiences a tactile warning signal upon approach of the snap action. This avoids surprise, and permits a more facile and accurate positioning of the dressing 256 on a patient. Different forms of warning signal may be developed by various arrangements of the dot regions 262, 264 and 266. For example, there may be alternation of the regions 262 and 266 to give a rapid repetition of strong and weak forces occurring immediately before the snap action.

Figure 29:
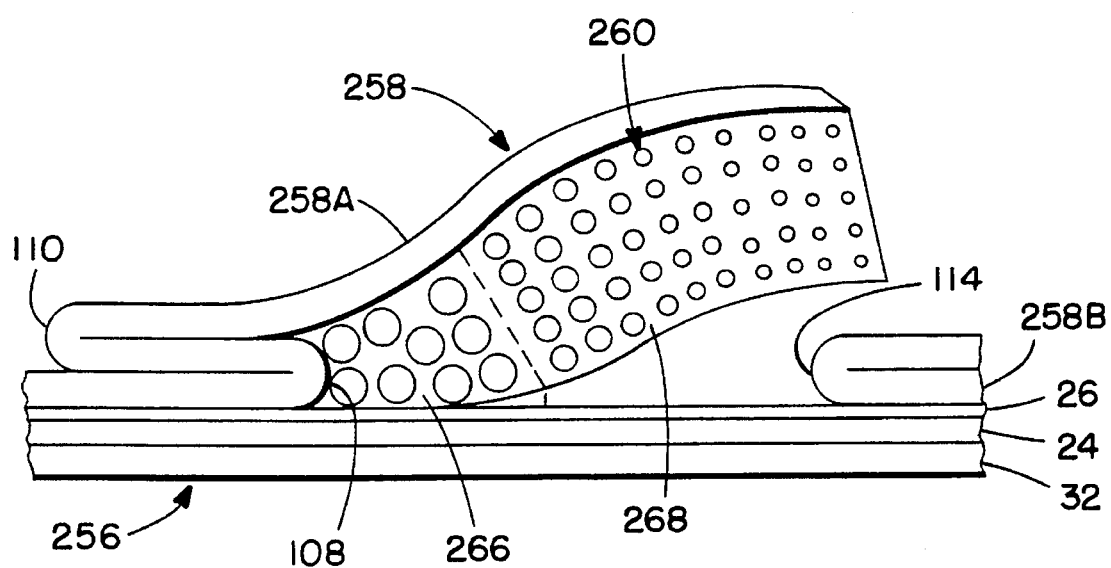

By way of further example, there may be a continuous variation in density of the dots of release coating as shown in region 268 of FIG. 29 to provide for a continuous variation in release force during a stage of withdrawal of the release sheet 258.

In yet a further embodiment of the invention, the region 266 of FIG. 28 may be fully coated with the release coating for minimal withdrawal force, and the region 264 may be replaced with more of the small-dot region 262. This would provide a form of snap action which precedes that of the opening of the fold 110. The snap action produced by the variation of the coating pattern can be employed even in the absence of the fold 108 and 110. Thus, this feature of release force variation by alteration of the coating pattern permits construction of a dressing, such as that of FIG. 28, without the folds 108 and 110 while still maintaining the snap-action characteristic.

In the practice of the invention as disclosed in the embodiments of FIGS. 12–15 and 27–28, the first section of release sheet (section 106A of FIG. 13 or section 258A of FIG. 28) extends from a first end of the dressing 104, 256 towards a second end of the dressing opposite the first end of the dressing, and the second section 106B, 258B of the release sheet extends from the second end of the dressing toward the first end of the dressing to meet the first section 106A, 258A of release sheet. The meeting of the two sections of release sheet accomplishes a covering of the adhesive layer 26 so as to avoid accidental contact by a nurse or physician with the adhesive layer 26. An adequate meeting of the two sections of release sheet is accomplished by abutment of the two sections of release sheet or by overlapping of the two sections of release sheet, this being a matter of convenience in manufacture. With respect to the abutment of the two sections of release sheet, there may be a slight spacing between the two sections of release sheet or physical contact between the two sections of release sheet, this being a matter of convenience in manufacture. With any of the foregoing configurations of the meeting of the two sections of release sheet, the snap-action or signaling of approach to the wound contacting region 252 is fully operative in the manner disclosed. In the preferred embodiment, the meeting is accomplished by overlap as shown in FIG. 13.

It is to be understood that the above described embodiments of the invention are illustrative only, and that modifications thereof may occur to those skilled in the art. Accordingly, this invention is not to be regarded as limited to the embodiments disclosed herein, but is to be limited only as defined by the appended claims.

What is claimed is:

1. A bandage to be placed on the skin of a patient, the bandage comprising a layer of elastomeric nonwoven fabric and an absorbent pad located on a side of the fabric facing the skin, the fabric having a density in the range of approximately 15–250 grams per square meter and a thickness in the range of approximately 0.05–0.75 millimeters, the fabric having a multidimensional recoverable elastic strain at least double an unstrained length of the fabric, there being a layer of adhesive on the side of the fabric facing the pad for securing the pad to the fabric, the adhesive serving to secure the bandage to the skin.

2. A bandage according to claim 1 further comprising a layer of film impervious to a liquid but pervious to a vapor of the liquid, the film being located on a side of said fabric opposite said pad, said film being bonded to said fabric.

3. A bandage to be placed on the skin of a patient, the bandage comprising:
a layer of elastomeric nonwoven fabric;
an absorbent pad bonded to the fabric on a first side of the fabric facing the skin, there being a layer of adhesive on said first side of the fabric for securing the bandage to the skin; and
a layer of film impervious to a liquid but pervious to a vapor of the liquid, the film being bonded to said fabric on a second side of said fabric opposite said first side.

4. A bandage according to claim 3 wherein said layer of fabric has a multidimensional recoverable elastic strain at least double an unstrained length of the fabric so as to be conformable to a human or animal body.

5. A moisture-vapor-permeable dressing for use on human and animal skin comprising:
a conformable elastomeric film permeable to water vapor but impermeable to liquid water;
a layer of conformable elastomeric fabric of nonwoven filamentary material bonded to said film to form therewith a composite laminated structure, said layer of nonwoven material having a discontinuous form open to a transpiration of water vapor at a rate substantially greater than the permeability of said film, said layer of nonwoven material having a recoverable elastic strain so as to be conformable to a human or animal body.

6. A breathable surgical dressing comprising:
a conformable elastomeric film permeable to water vapor but impermeable to liquid water;
a layer of conformable elastomeric fabric bonded to said film to form therewith a laminated structure; and
adhesive means disposed along a surface of said laminated structure for securing said dressing to the skin of a patient; and wherein
said adhesive means comprises a layer of adhesive material having multiple perforations therein to increase a capacity to breathe in the adhesive layer; and
said fabric comprises a breathable structure from a class of breathable structures consisting of nonwoven filamentary material and perforated sheet material, the fabric having passages for transpiration of water vapor, the fabric having a density in the range of approximately 15–250 grams per square meter and a thickness in the range of approximately 0.05–0.75 millimeters.

7. A dressing according to claim 6 wherein said layer of elastomeric fabric is a protective layer;
said adhesive means is disposed on a surface of said film opposite said protective layer;
said protective layer of fabric has a multidimensional recoverable elastic strain at least double an unstrained length of the fabric to be conformable to a patient's body; and wherein
said protective layer deforms more readily in response to an abrasive force than does a composite structure comprising said film, said adhesive and the skin secured by the adhesive to said film, thereby to distribute an abrasive force over the composite structure to inhibit tearing of said film.

8. A dressing according to claim 6 wherein said layer of elastomeric fabric is a protective layer;
said adhesive means is disposed of a surface of said film opposite said protective layer;
the bonding of said protective layer to said film provides for a releasable securing of said protective layer to said film; and
the bonding of said protective layer to said film is accomplished by a second breathable layer of adhesive, said second breathable layer of adhesive being disposed on a surface of said protective layer in a form of an array of spaced-apart islands of adhesive material to increase a capacity for breathing by said second breathable layer.

9. A dressing according to claim 8 wherein
said protective layer of fabric has a multidimensional recoverable elastic strain at least double an unstrained length of the fabric to be conformable to a patient's body;
said protective layer deforms more readily in response to an abrasive force than does a composite structure comprising said film, said adhesive and the skin secured by the adhesive to said film, thereby to distribute an abrasive force over the composite structure to inhibit tearing of said film.

10. A surgical dressing comprising:

a conformable elastomeric film permeable to water vapor but impermeable to liquid water;

a protective layer of conformable elastomeric fabric bonded to said film to form therewith a laminated structure, said protective layer of fabric having a multidimensional recoverable elastic strain at least double an unstrained length of the fabric to be conformable to a patient's body; and adhesive means disposed along said film on a side opposite said protective layer for securing said dressing to the flesh of a patient, and wherein said laminated structure together with said adhesive means are permeable to water vapor, said laminated structure being sufficiently elastic to conform to contours of the patient's flesh.

11. A dressing according to claim 10 wherein a portion of said protective layer is deleted to form a window exposing said film.

12. A surgical dressing comprising:

a conformable elastomeric film permeable to water vapor but impermeable to liquid water;

a protective layer of conformable elastomeric fabric bonded to said film to form therewith a laminated structure, said protective layer of fabric having a multidimensional recoverable elastic strain at least double an unstrained length of the fabric to be conformable to a patient's body; and adhesive means disposed along said film on a side opposite said protective layer for securing said dressing to the flesh of a patient, and wherein said laminated structure together with said adhesive means are permeable to water vapor, said laminated structure being sufficiently elastic to conform to contours of the patient's flesh; and wherein said film is transparent and a portion of said protective layer is deleted to form a window for viewing the patient's flesh beneath said film.

13. An air-permeable bandage for use on human and animal skin comprising:

absorptive pad means for absorbing exudate from the skin; and a layer of conformable elastomeric filamentary fabric secured to said absorptive pad means and having an adhesive layer for securing the bandage to the skin, said fabric layer having a discontinuous form open to a transpiration of water vapor and air with an open area greater than approximately 30% of the total surface area of the fabric layer, the fabric layer having a recoverable stretch in each of three dimensions in excess of approximately 100% and being constructed with a thickness in a range of 0.05 to 0.75 millimeters to permit unhindered skin function including a stretching of the skin during a bending of a limb of the human or the animal while protecting a region of the skin from an external environment.

14. A bandage according to claim 13 wherein a periphery of said fabric is formed in the shape of a cartoon-type of image.

15. A bandage according to claim 13 wherein said fabric is imprinted with a cartoon-type of image.

16. A bandage according to claim 15 wherein a periphery of said fabric is formed in the shape of a cartoon-type of image.

17. A breathable surgical dressing comprising:

a plurality of layer assemblies disposed one upon the other to produce a laminated structure, each of said layer assemblies comprising a conformable elastomeric film permeable to water vapor but impermeable to liquid water, and a protective layer of conformable elastomeric fabric bonded to said film; and wherein in each of said layer assemblies, said fabric comprises a breathable structure from a from a class of breathable structures consisting of nonwoven filamentary material and perforated sheet material, the fabric having passages for transpiration of water vapor, the fabric having a density in the range of approximately 15–250 grams per square meter and a thickness in the range of approximately 0.05–0.75 millimeters; and said dressing further comprises adhesive means disposed along the film in a first of said layer assemblies on a surface of the film opposite the protective layer of said assembly for securing said dressing to a patient; and at least one adhesive layer for securing each of successive ones of said assemblies to each other to form said laminated structure, successive adhesive layers providing successively smaller adhesive forces which are smaller than a force of said adhesive means to permit selective addition and subtraction of said layer assemblies from said laminated structure for adjusting a capacity of said dressing to breathe.

18. A breathable surgical dressing comprising:

a conformable elastomeric film permeable to water vapor but impermeable to liquid water;

a protective layer of conformable elastomeric fabric bonded to said film to form therewith a laminated structure; and adhesive means disposed along said film on a surface thereof opposite said protective layer for securing said dressing to the skin of a patient, said laminated structure being sufficiently elastic to conform to the contours of the patient's body; and wherein said fabric comprises a breathable structure from a class of breathable structures consisting of nonwoven filamentary material and perforated sheet material, the fabric having passages for transpiration of water vapor, the fabric having a density in the range of approximately 15–250 grams per square meter and a thickness in the range of approximately 0.05–0.75 millimeters;

the bonding of said protective layer to said film provides for a releasable securing of said protective layer to said film;

the bonding of said protective layer to said film is accomplished by a second breathable layer of adhesive, said second breathable layer of adhesive being disposed on a surface of said protective layer in a form of an array of spaced-apart islands of adhesive material to increase a capacity for breathing by said second breathable layer.

19. A dressing according to claim 18 wherein said protective layer of fabric has a multidimensional recoverable elastic strain at least double an unstrained length of the fabric to be conformable to a patient's body;

said protective layer deforms more readily in response to an abrasive force than does a composite structure comprising said film, said adhesive and the skin secured by the adhesive to said film, thereby to distribute an abrasive force over the composite structure to inhibit tearing of said film.

20. An air-permeable bandage for use on human and animal skin comprising:

absorptive pad means for absorbing exudate from the skin; and a layer of conformable elastomeric filamentary fabric secured to said absorptive pad means and having an adhesive layer for securing the bandage to the skin, said fabric layer having a discontinuous form open to a transpiration of water vapor and air with an open area greater than approximately 30% of the total surface area of the fabric layer, the fabric layer having a recoverable stretch in each of three dimensions in excess of approximately 100%; and indicia imprinted on said fabric, the indicia elongating during a stretching of said fabric to indicate an amount of tension in the fabric.

21. A dressing for urging together opposed edges of a break in the integument of a human being or an animal, the dressing comprising:

a layer of nonwoven fabric, said fabric being elastomeric and having a recoverable elastic strain at least double the unstrained length of the fabric; and means for securing said fabric to the integument.

22. A dressing according to claim 21 wherein said dressing further comprises indicia imprinted on said fabric, the indicia elongating during a stretching of said fabric to indicate an amount of tension in the fabric.

23. A dressing according to claim 22 wherein said dressing is suitable for covering a exudate which may be present on the integument; and said dressing further comprises a barrier of elastomeric material impermeable to the exudate on the integument but permeable to a vapor of the exudate, the barrier being embedded in interstices of the fabric.

24. A dressing according to claim 23 wherein said securing means is an adhesive layer disposed on a surface of said fabric; and said dressing further comprises a release sheet removably secured to said adhesive layer, removal of said release sheet exposing said adhesive layer for adhesively securing said fabric to the integument.

25. A dressing according to claim 22 wherein said dressing is suitable for covering an exudate which may be present on the integument; and said dressing further comprises a film of elastomeric material impermeable to the exudate on the integument but permeable to a vapor of the exudate, the film being secured to a surface of the fabric.

26. A dressing according to claim 25 wherein said securing means is an adhesive layer disposed on a surface of said film opposite said fabric; and said dressing further comprises a release sheet removably secured to said adhesive layer, removal of said release sheet exposing said adhesive layer for adhesively securing said fabric to the integument.

27. A vapor permeable dressing comprising:

a conformable elastomeric film permeable to water vapor but impermeable to liquid water;

a protective layer of conformable elastomeric fabric bonded to said film to form therewith a laminated structure, the protective layer of fabric having a multidimensional recoverable elastic strain at least double an unstrained length of the fabric to be conformable to a patient's body; and adhesive means disposed along said film on a side opposite said protective layer for securing said dressing to the flesh of a patient, the adhesive layer including a topical reagent disposed along a surface of the adhesive layer opposite said film, and wherein said laminated structure together with said adhesive means are permeable to water vapor, said laminated structure being sufficiently elastic to conform to contours of the patients flesh; and wherein said protective layer deforms more readily in response to an abrasive force than does a composite structure comprising a film, said adhesive means, and the skin secured by the adhesive means to said film, thereby to distribute an abrasive force over the composite structure to inhibit tearing of said film.

28. A dressing according to claim 27 wherein a portion of said protective layer is cutaway to form a window for viewing skin beneath said film.

29. A dressing according to claim 28 wherein said film is transparent, said dressing further comprising:

a section of protective layer of material adhesively securable about said window as a window shade for occluding a view of flesh beneath the window.

30. A vapor permeable dressing comprising:

a conformable elastomeric film permeable to water vapor but impermeable to liquid water;

adhesive means disposed along said film for securing said film to the flesh of a patient, said adhesive means being permeable to water vapor; and a release sheet removably securable to said film for detachment from said film prior to application of said dressing to the patient, said adhesive means being disposed between said film and said release sheet; and wherein said release sheet includes a topical reagent disposed along a surface of said release sheet facing said adhesive means, there being a bonding force securing said reagent to said release sheet and an attractive force between said reagent and said adhesive means, said attractive force being greater than said bonding force for retention of said reagent with said adhesive means upon a separation of said release sheet from said film.

31. A dressing according to claim 30 wherein said adhesive means comprises a layer of adhesive, said layer of adhesive being retained on said film upon a separation of said release sheet from said film.

32. A dressing according to claim 30 wherein said reagent is distributed uniformly along an interface between said release sheet and said adhesive means.

33. A dressing according to claim 30 wherein said reagent is disposed as a continuous coating on said release sheet.

34. A dressing according to claim 30 wherein said reagent is disposed as a random pattern on said release sheet.

35. A dressing according to claim 30 wherein said reagent is disposed as a periodic pattern on said release sheet.

36. A dressing according to claim 30 wherein said reagent is disposed uniformly along said release sheet, there being a marginal region of said release sheet which is free of said reagent.

37. A dressing according to claim 30 wherein said reagent is disposed along predetermined contours on said release sheet.

38. A dressing according to claim 30 wherein said film together with said adhesive means have a moisture-vapor-permeability greater than approximately 250 grams per square meter per 24 hour interval of time at a relative humidity of 80%.

39. A dressing for aseptic topical delivery of medication to a patient comprising:

a hydrophilic pad;

means for securing said pad to a site on the skin of a patient, said securing means including a window providing access to said pad for the delivery of liquid medication to the pad, contact of the pad with the skin providing for delivery of the medication from the pad via the skin to the patient; and hydrophilic filter means disposed between said window and said pad for admission of liquid medication to said pad while inhibiting ingress of microbial infection.

40. A dressing according to claim 39 further comprising cover means disposed on said securing means for closing said window to the environment.

41. A dressing according to claim 30 wherein said cover means is formed as a reservoir opening upon said filter means, said reservoir being suitable for a storage of medication and for allowing the medication to be delivered via said filter means to said pad.

42. A dressing according to claim 41 wherein said reservoir has an inlet port with a stopper therein, the stopper being pervious to a syringe needle for receipt of medication from the syringe into the reservoir.

43. A dressing according to claim 42 wherein said support is fabricated of a material which is impervious to liquid water, but is permeable to water vapor.

44. A breathable surgical dressing comprising:

a conformable elastomeric film permeable to vapor of a liquid but impermeable to the liquid;

adhesive means disposed along said film on a surface thereof for securing said dressing to the skin of a patient; and a release sheet removably secured to said adhesive means, said release sheet comprising a first section and a second section which overlap each other, said second section having at least one fold, said first section having two folds arranged in a reversing fold sequence to allow for a snap action at a location on said film upon release of a portion of the first section from said adhesive means during an uncovering of the adhesive means; and wherein said release sheet includes an arrangement of variable release force means for signaling an approach to said location.

45. A dressing according to claim 44 wherein said second section of release sheet comprises a reversing fold sequence including said at least one fold, a portion of said first section of release sheet extending across a central portion of said adhesive means to overlap a corresponding portion of said second section of release sheet, the reversing fold sequence of said second section of release sheet providing a snap action upon a separating of said second section of release sheet from the central portion of said adhesive means.

46. A dressing according to claim 44 further comprising a protective layer of conformable elastomeric fabric bonded to said film to form therewith a laminated structure; and wherein said liquid is water, and said fabric comprises a breathable structure from a class of breathable structures consisting of nonwoven filamentary material and perforated sheet material, the fabric having passages for transpiration of water vapor, the fabric having a density in the range of approximately 15–250 grams per square meter and a thickness in the range of approximately 0.05–0.75 millimeters.

47. A dressing according to claim 46 wherein said protective layer of fabric has a multidimensional recoverable elastic strain at least double an unstrained length of the fabric to be conformable to a patient's body.

48. A dressing according to claim 47 wherein said protective layer deforms more readily in response to an abrasive force than does a composite structure comprising said film, said adhesive means and the skin secured by said adhesive means to said film, thereby to distribute an abrasive force over the composite structure to inhibit tearing of said film.

49. A breathable surgical dressing comprising:

a conformable elastomeric film having a first end and a second end opposite said first end, said film being permeable to vapor of a liquid but impermeable to the liquid, a portion of said film serving as a wound contacting region;

adhesive means disposed on a surface of said film for securing said dressing to the skin of a patient;

a release sheet removably secured to said adhesive means, said release sheet comprising a first section extending from said first end toward said second end, and a second section extending from said second end toward said first end to meet said second section;

means on at least one of said sections of release sheet for varying a release force to provide a snap action at a location on said film distant from said first and said second ends and independent of a position of said wound contacting region.

50. A dressing according to claim 49 wherein said force varying means provides for a reduction of release force via a plurality of stages of withdrawal of said at least one section of release sheet.

51. A dressing according to claim 50 wherein said force varying means is operative to produce a continuous variation of release force during one of said stages.

52. A dressing according to claim 49 wherein said first and said second sections of release sheet overlap each other.

53. A dressing according to claim 49 wherein said force varying coating means is operative to produce a continual variation of release force.

54. A dressing according to claim 49 wherein said force varying coating means comprises a coating disposed on said at least one section of release sheet in various states of curing.

55. A dressing according to claim 49 wherein said force varying coating means comprises a coating disposed on said at least one section of release sheet in an array of dots of various spacings.

56. A dressing according to claim 49 wherein said force varying coating means comprises a coating disposed on said at least one section of release sheet in an array of dots of varying sizes.

57. A dressing according to claim 49 wherein said force varying coating means comprises a coating disposed on said at least one section of release sheet in an array of dots of varying spacing and sizes.

58. A breathable surgical dressing comprising:

a conformable elastomeric film having a first end and a second end opposite said first end, said film being permeable to water vapor but impermeable to liquid water, a portion of said film serving as a wound contacting region;

adhesive means disposed on a surface of said film for securing said dressing to the skin of a patient;

a release sheet removably secured to said adhesive means, said release sheet comprising a first section extending from said first end toward said second end, and a second section extending from said second end toward said first end to meet said second section;

means on at least one of said sections of release sheet for varying a release force to provide a snap action at a location on said film distant from said first and said second ends and independent of a position of said wound contacting region; wherein said force varying means provides for a reduction of release force via a plurality of stages of withdrawal of said at least one section of release and is operative to produce a continuous variation of release force during one of said stages.

* * * * *